United States Patent [19]
Jakobi et al.

[11] Patent Number: 5,852,042
[45] Date of Patent: Dec. 22, 1998

[54] SUBSTITUTED PYRIDINES, PROCESSES FOR THEIR PREPARATION AND THEIR USE AS PESTICIDES AND FUNGICIDES

[75] Inventors: Harald Jakobi, Frankfurt; Werner Knauf, Eppstein; Ulrich Sanft, Hofheim; Manfred Kern, Lörzweiler; Dieter Bernd Reuschling, Butzbach; Adolf Heinz Linkies, Franfurt; Werner Bonin, Kelkheim, all of Germany

[73] Assignee: Hoechst Schering AgrEvo GmbH, Berlin, Germany

[21] Appl. No.: 534,238

[22] Filed: Sep. 26, 1995

[30] Foreign Application Priority Data

Sep. 28, 1994 [DE] Germany ............ 44 34 637.9

[51] Int. Cl.$^6$ .................... C07D 413/12; C07D 213/68; A01N 43/40; A01N 43/42
[52] U.S. Cl. .................. 514/352; 514/344; 514/348; 514/349; 546/288; 546/289; 546/296; 546/197; 546/309
[58] Field of Search .................. 546/297, 309, 546/288, 289, 296; 514/349, 355, 344, 348

[56] References Cited

U.S. PATENT DOCUMENTS 5,358,957  10/1994  Maienfisch et al. ............ 514/342

FOREIGN PATENT DOCUMENTS

| 0436348 | 7/1991 | European Pat. Off. . |
| 0540472 | 5/1993 | European Pat. Off. . |
| 0314427 | 5/1989 | WIPO . |
| WO 82/00401 | 2/1992 | WIPO . |
| WO 93/04580 | 3/1993 | WIPO . |

OTHER PUBLICATIONS

Chemical Abstracts 87:177685, RN 64303.89–5, 1977.
Chemical Abstracts, vol. 112, No. 7, Feb. 12, 1990, p. 739, column 1, Abstract No. 5555 4v.
Chemical Abstracts, vol. 77, No. 1, Jul. 3, 1972, p. 34, column 1, Abstract No. 341b.
Chemical Abstracts, vol. 103, No. 13, Sep. 30, 1985, p. 608, column 1, Abstract No. 104819k.
Chemical Abstracts, vol. 55, No. 25, Dec. 11, 1961, Abstract No. 25943i.
Chemical Abstracts, vol. 72, No. 15, Apr. 13, 1970, p. 124, column 1, Abstract No. 76012n.

*Primary Examiner*—Zinna Northington Davis
*Attorney, Agent, or Firm*—Frommer Lawrence & Haug LLP

[57] ABSTRACT

The invention relates to novel substituted N-(4-pyridyl) carboxamides of the formula

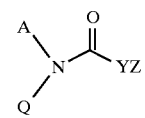

in which Q is substituted 4-pyridyl, A is hydrogen, alkyl, acyl or aralkyl and Y-Z is an optionally modified hydrocarbon radical or Y is a bond or a bivalent radical and Z is aryl, O-aryl, cycloalkyl, cycloalkenyl or heterocyclyl, all of which are optionally substituted, to processes for their preparation, to intermediates during their preparation, and to their use as pesticides, in particular as insecticides, acaricides and nematicides, and also as fungicides.

16 Claims, No Drawings

SUBSTITUTED PYRIDINES, PROCESSES FOR THEIR PREPARATION AND THEIR USE AS PESTICIDES AND FUNGICIDES

The invention relates to novel substituted N-(4-pyridyl) carboxamides, to processes for their preparation, and to their use as pesticides, in particular as insecticides, acaricides and nematicides, and also as fungicides.

It has already been disclosed that certain substituted N-(4-pyridyl)arylacetamides have a fungicidal, acaricidal, insecticidal and nematicidal action (cf. WO 93/04580). However, the biological action of these compounds is not entirely satisfactory in all fields of application, in particular when low rates and concentrations are applied.

There have been found novel substituted N-(4-pyridyl) carboxamides of the formula I which have a biological activity.

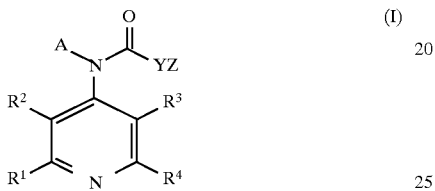

The invention therefore relates to compounds of the formula I and to their N-oxides and salts, in which (1) (a) $R^1$ is $(C_2-C_4)$alkenyl, $(C_2-C_4)$alkynyl, $(C_3-C_7)$cycloalkenyl, $(C_2-C_4)$-alkenyloxy, $(C_2-C_4)$alkynyloxy, $(C_3-C_7)$cycloalkenyloxy, halo$(C_2-C_4)$alkenyl, halo$(C_3-C_7)$cycloalkyl, halo$(C_2-C_4)$alkenyloxy, halo$(C_3-C_7)$cycloalkyloxy, R—O$(C_1-C_4)$alkyl, R—O—CO—, R—CO—, formyl, halo$(C_1-C_4)$alkoxy$(C_1-C_4)$alkyl, halo$(C_1-C_4)$alkoxyhalo$(C_1-C_4)$alkyl, $(C_1-C_4)$alkoxyhalo$(C_1-C_4)$alkyl, halo$(C_1-C_4)$alkoxycarbonyl, halo$(C_2-C_4)$alkenyloxy$(C_1-C_4)$alkyl, halo$(C_2-C_4)$alkenyloxycarbonyl, $(C_3-C_7)$cycloalkylthio, halo$(C_1-C_4)$alkylthio, $(C_3-C_7)$cycloalkylsulfinyl, halogen$(C_1-C_4)$alkylsulfinyl, $(C_3-C_7)$cycloalkylsulfonyl, halo$(C_1-C_4)$alkylsulfonyl, $(C_2-C_4)$alkenylthio, $(C_3-C_7)$cycloalkenylthio, $(C_2-C_4)$alkenylsulfinyl, $(C_3-C_7)$cycloalkenylsulfinyl, $(C_2-C_4)$alkenylsulfonyl, $(C_3-C_7)$cycloalkenylsulfonyl, iodine, cyano, cyano$(C_1-C_4)$alkyl, nitro, thiocyanato, $(C_1-C_4)$alkylthio$(C_1-C_4)$alkyl, $(C_2-C_4)$alkenylthio$(C_1-C_4)$alkyl, halo$(C_1-C_4)$alkylthio$(C_1-C_4)$alkyl, $(C_1-C_4)$alkylthio-halo$(C_1-C_4)$alkyl, halo$(C_1-C_4)$alkylthio-halo$(C_1-C_4)$alkyl or halo$(C_2-C_4)$alkenylthio$(C_1-C_4)$alkyl; and $R^2$ is hydrogen or is as defined above for $R^1$; or, if not embraced by the above definitions, (b) $R^1$ is as defined for $R^2$ under (a); and $R^2$ is as defined for $R^1$ under (a); or, if not embraced by the above definitions, (c) $R^1$ is $(C_1-C_4)$alkylthio, $(C_1-C_4)$alkylsulfinyl or $(C_1-C_4)$alkylsulfonyl, or is as defined for $R^1$ under (a); and $R^2$ is $(C_1-C_4)$alkylthio, $(C_1-C_4)$alkylsulfinyl, $(C_1-C_4)$alkylsulfonyl, fluorine, chlorine, bromine, $(C_1-C_4)$alkyl, halo$(C_1-C_4)$alkyl, $(C_3-C_7)$cycloalkyl, $(C_1-C_4)$alkoxy or halo$(C_1-C_4)$alkoxy, or is as defined for $R^1$ under (a); or, if not embraced by the above definitions, (d) $R^1$ is as defined for $R^2$ under (c); and $R^2$ is as defined for $R^1$ under (c);

(e) $R^3$ and $R^4$ are identical or different and independently of one another are hydrogen, halogen, $(C_1-C_4)$alkyl, $(C_1-C_4)$haloalkyl, $(C_3-C_5)$cycloalkyl and/or halo$(C_3-C_5)$cycloalkyl;

(f) R is $(C_1-C_{10})$alkyl, $(C_2-C_{10})$alkenyl, $(C_2-C_{10})$alkynyl, $(C_3-C_8)$cycloalkyl or aralkyl, (g) A is hydrogen, $(C_1-C_4)$alkyl, $(C_1-C_4)$acyl or aralkyl; aryl is as defined under (4) (a), and aralkyl is aryl $(C_1-C_4)$alkyl;

(2) Y-Z together is a $(C_1-C_{15})$-hydrocarbon radical which is unbranched or branched and in which one or more, preferably up to three, $CH_2$ groups can be replaced by heteroatom groups, such as O, $NR^5$, S, SO, $SO_2$ or $SiR^6R^7$, where $R^5$ is hydrogen, $(C_1-C_4)$alkyl or $(C_1-C_4)$acyl, and $R^6$ and $R^7$, which are identical or different, independently of one another are $(C_1-C_4)$alkyl, phenyl and/or substituted phenyl, and where the above $(C_1-C_{15})$ hydrocarbon radical, with or without the abovementioned variations which are possible (replacement by a heteroatom group, or heteroatom groups) is optionally substituted by one or more, preferably up to three, identical or different radicals selected from the group consisting of $(C_1-C_7)$alkyl, $(C_2-C_4)$alkenyl, $(C_2-C_4)$alkynyl, $(C_3-C_7)$cycloalkyl, $(C_3-C_7)$cycloalkenyl, halogen, halo-$(C_1-C_4)$alkyl, halo$(C_3-C_7)$cycloalkyl, halo$(C_1-C_4)$alkoxy, halo$(C_3-C_7)$cycloalkoxy, hydroxyl, cyano and $(C_1-C_4)$acyl;

or, if not embraced by the above definitions, (3) Y is a bond or a bivalent hydrocarbon radical having 1 to 6 carbon atoms which is optionally substituted by one or more, preferably up to three, identical or different radicals selected from the group consisting of $(C_1-C_7)$alkyl, $(C_2-C_4)$alkenyl, $(C_3-C_7)$alkynyl, $(C_3-C_7)$cycloalkyl, $(C_3-C_7)$cycloalkenyl, halogen, halo$(C_1-C_4)$alkyl, halo$(C_3-C_7)$cycloalkyl, halo$(C_1-C_4)$alkoxy, halo$(C_3-C_7)$cycloalkoxy, hydroxyl, cyano and $(C_1-C_4)$acyl; and (4) Z (a) is aryl, where aryl is a phenyl group which is optionally substituted by one or more, preferably up to five, in particular up to three, identical or different radicals selected from the group consisting of halogen, $(C_3-C_8)$cycloalkyl, $(C_3-C_8)$cycloalkenyl, phenoxy, substituted phenoxy, phenylthio, substituted phenylthio, phenyl, substituted phenyl, nitro, —CO—$R^8$, acetoxy, hydroxyl, cyano, $SiR^9R^{10}R^{11}$, O—$SiR^9R^{10}R^{11}$, $NR^{12}R^{13}$, $S(O)R^{14}$, $SO_2R^{14}$, $(C_1-C_{12})$alkyl, $(C_2-C_{12})$alkenyl, $(C_1-C_{12})$alkoxy, $(C_3-C_7)$cycloalkoxy, $(C_1-C_{12})$alkylthio and $(C_3-C_7)$cycloalkylthio, where in the above $(C_1-C_{12})$alkyl, $(C_2-C_{12})$alkenyl, $(C_1-C_{12})$alkoxy and $(C_1-C_{12})$alkylthio radicals one or more, preferably up to 3, $CH_2$ groups are optionally replaced by CO and/or heteroatoms or heteroatom groups, such as O, S, SO, $SO_2$, $NR^5$ or $SiR^6R^7$; and where the above $(C_1-C_{12})$alkyl, $(C_1-C_{12})$alkenyl, $(C_1-C_{12})$alkoxy and $(C_1-C_{12})$alkylthio groups, with or without the abovementioned variations which are possible (replacement by CO and/or a heteroatom group, or heteroatom groups), can have attached to them one or more, preferably up to three, in the case of halogen up to the maximum number of, identical or different radicals selected from the group consisting of halogen, halo $(C_1-C_4)$alkoxy, hydroxyl, $(C_3-C_8)$cycloalkyl, $(C_3-C_8)$cycloalkenyl, $(C_1-C_4)$acyl, phenyl, substituted phenyl, phenoxy, substituted phenoxy, phenylthio and substituted phenylthio; and $R^5$, $R^6$ and $R^7$ are as defined above under (2);

$R^8$ is $(C_1-C_7)$alkyl, halo$(C_1-C_7)$alkyl, $(C_3-C_7)$cycloalkyl, halo$(C_3-C_7)$cycloalkyl, $(C_1-C_7)$alkoxy, $(C_1-C_7)$alkylthio, phenyl or substituted phenyl;

$R^9$, $R^{10}$ and $R^{11}$ are identical or different and independently of one another are $(C_1-C_4)$alkyl, phenyl and/or substituted phenyl;

$R^{12}$ and $R^{13}$ are identical or different and independently of one another are hydrogen, $(C_1-C_4)$alkyl and/or $(C_1-C_4)$acyl;

$R^{14}$ is $(C_1-C_{10})$alkyl, phenyl or substituted phenyl; or (b) can also be O-aryl if Y is not a direct bond; aryl being as defined above under (4) (a); or (c) is $(C_3-C_8)$cycloalkyl or $(C_5-C_8)$cycloalkenyl, it being possible for one $CH_2$ group of the carbocycle to be replaced by $NR^{15}$, and $R^{15}$ is phenyl or substituted phenyl; and the abovementioned $(C_3-C_8)$cycloalkyl or $(C_5-C_8)$cycloalkenyl is optionally substituted by one or more, preferably up to three, in the case of halogen up to the maximum number of, identical or different radicals selected from the group consisting of $(C_1-C_{18})$alkyl, $(C_2-C_{18})$alkenyl, $(C_2-C_{18})$alkynyl, $(C_1-C_{12})$alkoxy, $(C_1-C_{12})$alkanoyloxy, $(C_2-C_{12})$acyl, $(C_1-C_{12})$alkyloxycarbonyl, $(C_2-C_{18})$alkanediyl, $(C_1-C_{18})$alkanediyldioxy, $(C_1-C_{13})$alkyloximino, $(C_1-C_{18})$alkylidene, $SiR^9R^{10}R^{11}$, $NR^{16}R^{17}$, hydroxyl, oxo, halogen or aryl and it being possible for one or more, preferably up to three $CH_2$ groups in the first 11 hydrocarbon radicals mentioned above to be replaced by heteroatoms or heteroatom groups, such as O, S, SO, $SO_2$, $NR^5$ or $SiR^6R^7$, where $R^5$, $R^6$ and $R^7$ are as defined under (2) and where additionally three to six carbon atoms of these hydrocarbon radicals can form a cycle and these hydrocarbon radicals, with or without the variations (replacement of $CH_2$ and/or cyclization), are additionally optionally substituted by one or more, preferably up to three, in the case of halogen up to the maximum number of, identical or different radicals selected from the group consisting of halogen, haloalkyl, preferably having up to 6 carbon atoms, cycloalkyl, preferably having 3–7 carbon atoms, acyl, preferably having up to 6 carbon atoms, phenoxy, substituted phenoxy, phenyl, substituted phenyl, phenylthio and substituted phenylthio; $R^9$, $R^{10}$, $R^{11}$ and aryl are as defined under (4) (a); and $R^{16}$ and $R^{17}$ are identical or different and independently of one another are $(C_1-C_4)$acyl, $(C_3-C_6)$cycloalkyl, phenyl and/or substituted phenyl; or (d) is a furyl radical of the formula II

in which $R^{18}$ is hydrogen, halogen, halo$(C_1-C_4)$alkyl, cyano, nitro, $(C_1-C_4)$alkyl, phenyl, $(C_1-C_4)$alkoxy or halo$(C_1-C_4)$alkoxy; or (e) is a thienyl radical of the formula III

in which $R^{19}$ is hydrogen, halogen, halo$(C_1-C_4)$alkyl, cyano, nitro, $(C_1-C_4)$alkyl, phenyl, $(C_1-C_4)$alkoxy, halo$(C_1-C_4)$alkoxy or thienyl; or (f) if not embraced by the above definitions, is a radical of the formula IV or V

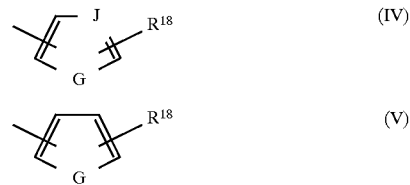

in which $R^{18}$ is as defined above under (4) (d), J is N or CH and G is O, $NR^{20}$ or S, with the proviso that, if J≠N, then G is $NR^{20}$, where $R^{20}$ is hydrogen, $(C_1-C_4)$alkyl, $(C_1-C_4)$acyl, phenylsulfonyl or substituted phenylsulfonyl; or (g) is a radical selected from the group consisting of optionally substituted naphthyl, dihydronaphthyl, tetrahydronaphthyl and decahydronaphthyl;
optionally substituted indolyl;
1,3-benzodioxolyl, 2,6-dimethyl-4-morpholinyl and 1-adamantyl; or (h) is a radical of the formula VI

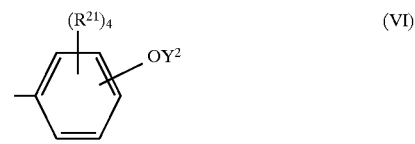

in which $R^{21}$ radicals are identical or different and independently of one another are hydrogen, halogen, $(C_1-C_4)$alkyl, $(C_1-C_4)$alkoxy, halo$(C_1-C_4)$alkyl, halo$(C_1-C_4)$alkoxy, $NO_2$, CN, $(C_1-C_4)$alkylcarbonyl, formyl, phenoxy and/or substituted phenoxy, with the proviso that at least two of the radicals $R^{21}$ are selected from the group consisting of hydrogen and fluorine.

and $Y^2$ is pyridyl, pyrazinyl, pyrimidinyl, pyridazinyl, triazinyl, benzoxazolyl or benzothiazolyl, each of which is optionally substituted by one or more, preferably up to three, identical or different radicals selected from the group consisting of halogen, $(C_1-C_4)$alkyl, $(C_1-C_4)$alkoxy, halo$(C_1-C_4)$alkyl, halo$(C_1-C_4)$alkoxy, nitro, cyano and $(C_1-C_4)$alkanoyl substituted; or (i) is a radical of the formula VII

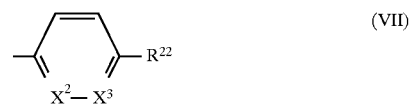

in which one of the groups $X^2$ or $X^3$ is N and the other group is CH;
$R^{22}$ is —W—$R^{23}$, phenyl or substituted phenyl;
W is O or S; and
$R^{23}$ is $(C_1-C_7)$alkyl, halo$(C_1-C_7)$alkyl, $(C_1-C_7)$alkoxy, halo$(C_1-C_7)$alkoxy, naphthyl or phenyl, where, if not embraced by the above definitions, each of the abovementioned radicals can be substituted by one or more, preferably up to three, in the case of halogen up to the maximum number of, identical or different radicals selected from the group consisting of halogen, $(C_1-C_{10})$alkyl, halo$(C_1-C_7)$alkyl, hydroxy $(C_1-C_7)$alkyl, $(C_1-C_4)$alkoxymethyl, $(C_1-C_4)$alkoxy, halo$(C_1-C_4)$alkoxy, phenoxy, substituted phenoxy, phenyl, substituted phenyl, cyano, nitro, hydroxyl, $(C_1-C_4)$alkanoyloxy or benzyloxy.

In the above formulae I to VII and hereinbelow—unless otherwise defined specifically—"halogen" is to be understood as meaning a fluorine, chlorine, bromine or iodine atom, preferably a fluorine, chlorine or bromine atom, in particular a fluorine or chlorine atom;

the term "alkyl" is to be understood as meaning an unbranched or branched hydrocarbon radical, such as, for example, the methyl, ethyl, propyl, 1-methylethyl, 1-methylpropyl, 2-methylpropyl or 1,1-dimethylethyl radical, the pentyl, 2-methylbutyl or 1,1-dimethylpropyl radical, the hexyl, heptyl or octyl radical, the 1,1,3,3-tetramethylbutyl radical, the nonyl, decyl, undecyl or dodecyl radical, and the like;

the terms "alkenyl" and "alkynyl" are to be understood as meaning the unsaturated radicals derived from these alkyl radicals;

the term "alkoxy" is to be understood as meaning an alkoxy group whose hydrocarbon radical is as defined under the term "alkyl";

the term "cycloalkyl" is to be understood as meaning preferably the cyclopropyl, cyclobutyl, cyclopentyl, cyclohexyl, cycloheptyl or cyclooctyl group;

the term "cycloalkenyl" is to be understood as meaning an unsaturated radical derived from these cycloalkyl radicals;

the term "cycloalkoxy" is to be understood as meaning a cycloalkoxy group whose hydrocarbon radical is as defined under "cycloalkyl";

the term "alkylthio" is to be understood as meaning an alkylthio group whose hydrocarbon radical is as defined under the term "alkyl;

the term "haloalkyl" is to be understood as meaning an alkyl group as in the term "alkyl" in which one or more hydrogen atoms is replaced by the abovementioned halogen atoms, preferably chlorine or fluorine, such as, for example, the trifluoromethyl group, the 2,2,2-trifluoroethyl group, the chloromethyl group, the fluoromethyl group, the difluoromethyl group or the 1,1,2,2-tetrafluoroethyl group (the same applies analogously to "haloalkenyl", "halocycloalkyl" and "halocycloalkenyl").

the term "haloalkoxy" is to be understood as meaning a haloalkoxy group whose halohydrocarbon radical is as defined under the term "haloalkyl"; in other radicals with the prefix "halo" which are not mentioned specifically herein, this prefix denotes, again, that one, several or all hydrogen atoms in these radicals are replaced by halogen atoms;

the term "substituted phenyl" is to be understood as meaning a phenyl radical which has attached to it one or more, preferably up to three, in the case of halogen up to the maximum number of, identical or different substituents from the series consisting of $(C_1-C_{10})$alkyl, halo$(C_1-C_7)$alkyl, hydroxy$(C_1-C_7)$alkyl, $(C_1-C_7)$alkoxy, halo$(C_1-C_7)$alkoxy, phenoxy, phenyl, nitro, hydroxyl, cyano, $(C_1-C_4)$alkanoyl, benzoyl, $(C_1-C_4)$alkanoyloxy, $(C_1-C_4)$alkoxycarbonyl, halogen, substituted phenoxy, substituted phenyl, phenoxycarbonyl and benzyloxy;

the term "substituted phenoxy" is to be understood as meaning a phenoxy group whose phenyl group is as defined under "substituted phenyl";

"substituted phenylthio" is to be understood as meaning a phenylthio group whose phenyl group is as defined under "substituted phenyl";

the term "substituted naphthyl" is to be understood as meaning a naphthyl radical which has attached to it one or more, preferably up to three, identical or different substituents selected from the group consisting of halogen, halo$(C_1-C_4)$alkyl, cyano, nitro, $(C_1-C_4)$alkyl, phenyl, $(C_1-C_4)$alkoxy and halo$(C_1-C_4)$alkoxy (the same also applies analogously to partially or fully hydrogenated naphthyl radicals);

the term "substituted indolyl" is to be understood as meaning an indolyl radical which has attached to it one or more, preferably up to three, identical or different substituents selected from the group consisting of halogen, halo$(C_1-C_4)$alkyl, cyano, nitro, $(C_1-C_4)$alkyl, phenyl, $(C_1-C_4)$alkoxy and halo$(C_1-C_4)$alkoxy;

the term "substituted amino" is to be understood as meaning an amino group which is substituted by one or two $(C_1-C_4)$alkyl groups or one $(C_1-C_4)$alkanoyl group;

a "hydrocarbon radical" is to be understood as meaning a radical derived from methane or straight-chain or branched alkanes by removing a hydrogen atom, it being possible for this radical, in the case of two and more carbon atoms, to include one or more double and/or triple bonds;

a "bivalent hydrocarbon radical" is to be understood as meaning a radical derived from n-alkanes or n-alkenes by removing in each case one hydrogen atom from the two terminal carbon atoms of the chain, such as methylene, ethanediyl, trimethylene or tetramethylene;

"acyl" is to be understood as meaning, in particular, an alkanoyl radical, such as acetyl, propionyl or butyryl, or an alkyloxycarbonyl radical.

The explanation given above applies analogously to homologs or to radicals derived therefrom.

The substituents on the cycloalkyl or cycloalkenyl radicals defined under (4) (c) can be in the cis or the trans position relative to Y; the cis position is preferred. If only one substitutent is present, it should preferably be in the 4-position in cyclohexyl.

Preferred compounds of the formula I and their N-oxides and salts are those in which at least one of the radicals $R^1$ and $R^2$, which are identical or different, is halocyclopropyl, $(C_1-C_2)$alkoxymethyl, halomethoxymethyl, halomethoxyhalomethyl, methoxyhalomethyl, iodine and/or cyano;

and in the event that only one radical $R^1$ and $R^2$ is as defined above, the other radical is hydrogen, fluorine, chlorine, bromine, $(C_1-C_4)$alkyl, halo$(C_1-C_2)$alkyl, cyclopropyl, methoxy or ethoxy;

$R^3$ and $R^4$, which are identical or different, independently of one another are defined as hydrogen or fluorine;

A is hydrogen and Y and Z are as defined above under (2) to (5);

in particular those compounds in which at least one of the radicals $R^1$ and $R^2$, which are identical or different, is methoxymethyl, iodine and/or cyano;

and in the event that only one radical $R^1$ or $R^2$ is as defined above, the other radical is chlorine, bromine, ethyl, propyl, isopropyl, trifluoromethyl or methoxy;

$R^3$, $R^4$ and A are in each case hydrogen and Y and Z are as defined above under (2) to (5).

Equally preferred are compounds of the formula I and their N-oxides and salts in which (1) $R^1$, $R^2$, $R^3$, $R^4$ and A are as defined above under (1); and
(2) Y-Z together is a hydrocarbon radical as defined above which is optionally substituted by one or more, preferably up to three, identical or different radicals selected from the group consisting of $(C_1-C_4)$alkyl, halogen, halo$(C_1-C_4)$ alkyl and halo$(C_1-C_4)$alkoxy;
  or, if not embraced by the above definitions;
(3) Y is a bond or a bivalent hydrocarbon radical having 1 to 4 carbon atoms which is optionally substituted by one or more, preferably up to three, identical or different radicals selected from the group consisting of $(C_1-C_4)$alkyl, halogen, halo$(C_1-C_4)$alkyl and halo$(C_1-C_4)$alkoxy; and
(4) Z
  (a) is aryl, where aryl is a phenyl group which is optionally substituted by one or more, preferably up to five, in particular up to three, identical or different radicals selected from the group consisting of halogen, $(C_3-C_8)$cycloalkyl, phenoxy, substituted phenoxy, phenylthio, substituted phenylthio, phenyl, substituted phenyl, $(C_1-C_{12})$alkyl, $(C_2-C_{12})$alkenyl, $(C_1-C_{12})$alkoxy and $(C_1-C_{12})$alkylthio, where in the above $(C_1-C_{12})$alkyl, $(C_2-C_{12})$alkenyl, $(C_1-C_{12})$alkoxy and $(C_1-C_{12})$alkylthio one or more, preferably up to 3, $CH_2$ groups are optionally replaced by CO and/or hetero atoms or heteroatom groups, such as O, S, SO, $SO_2$, $NR^5$ or $SiR^6R^7$; and where the above $(C_1-C_{12})$alkyl, $(C_1-C_{12})$alkenyl, $(C_1-C_{12})$alkoxy and $(C_1-C_{12})$alkylthio radicals, with or without the abovementioned variations which are possible (replacement by CO and/or a heteroatom group, or heteroatom groups), can have attached to them one or more, preferably up to two, in the case of halogen up to the maximum number of, identical or different radicals selected from the group consisting of halogen, phenyl, substituted phenyl, phenoxy, substituted phenoxy, phenylthio and substituted phenylthio; and
  $R^5$, $R^6$ and $R^7$ are as defined above under (2); or
  (b) can also be O-aryl if Y is not a direct bond; aryl being as defined above under (4) (a); or
  (c) is cyclohexyl which is substituted by one or more radicals, preferably by a radical selected from the group consisting of $(C_1-C_{18})$alkyl, $(C_2-C_{18})$alkenyl, $(C_2-C_{18})$alkynyl, $(C_1-C_{12})$alkoxy, $(C_1-C_{12})$alkanoyloxy, $(C_1-C_{12})$alkyloxycarbonyl, $SiR^9R^{10}R^{11}$ and aryl and it being possible for one or more, preferably up to three, $CH_2$ groups in the first 6 hydrocarbon radicals mentioned above to be replaced by O, and in which furthermore 3 to 6 carbon atoms of these hydrocarbon radicals can form a cycle;
  $R^9$, $R^{10}$ and $R^{11}$ are as defined at the outset under (4) (a) and aryl is as defined above;
  (d) a radical selected from the group consisting of optionally substituted naphthyl and optionally substituted tetrahydronaphthyl;
  (e) a radical of the formula VI in which $R^{21}$ radicals are identical or different and independently of one another are hydrogen, halogen and/or methyl, with the proviso that at least two of the radicals $R^{21}$ are selected from the group consisting of hydrogen and fluorine;
  and $Y^2$ is pyridyl, pyrazinyl, pyrimidinyl, pyridazinyl, triazinyl, benzoxazolyl or benzothiazolyl, which are optionally substituted by one or more, preferably up to three, identical or different radicals selected from the group consisting of halogen, methyl, methoxy and trifluoromethyl;
in particular those compounds of the formula I in which
  (1) $R^1$, $R^2$, $R^3$, $R^4$ and A are as defined above under (1); and
  (2) Y-Z together is a $(C_1-C_{15})$ hydrocarbon radical which is unbranched or branched and in which one or more, preferably up to three, $CH_2$ can be replaced by heteroatom groups, such as O or S,
    and where the above $(C_1-C_{15})$ hydrocarbon radical, with or without the abovementioned variations which are possible (replacement by a heteroatom group, or heteroatom groups) is optionally substituted by one or more, preferably up to three, identical or different radicals selected from the group consisting of methyl, ethyl, fluorine, chlorine and trifluoromethyl;
  or, if not embraced by the above definitions;
(3) Y is a bond or a bivalent hydrocarbon radical having 1 to 2 carbon atoms which is substituted by one or more, preferably up to three, identical or different radicals selected from the group consisting of methyl, ethyl, fluorine, chlorine and trifluoromethyl; and
(4) Z
  (a) is aryl, where aryl is a phenyl group which is optionally substituted by one or more, preferably up to five, in particular up to three, identical or different radicals from the group consisting of phenoxy, substituted phenoxy, phenylthio, substituted phenylthio, $(C_1-C_{12})$alkoxy and $(C_1-C_{12})$alkylthio, where in the above $(C_1-C_{12})$alkoxy and $(C_1-C_{12})$alkylthio one or more, preferably up to 3, $CH_2$ groups are optionally replaced by O; and where the above $(C_1-C_{12})$alkoxy and $(C_1-C_{12})$alkylthio, with or without the abovementioned variations which are possible (replacement by O) can have attached to them one or more, preferably one, in the case of halogen up to the maximum number of, identical or different radicals selected from the group consisting of halogen, phenyl, substituted phenyl, phenoxy and substituted phenoxy; or
  (b) can also be O-aryl if Y is not a direct bond; aryl being as defined above under (4) (a); or
  (c) is cyclohexyl which is substituted in the 4-position by a radical selected from the group consisting of $(C_3-C_{18})$alkyl or aryl and aryl is as defined under (4) (a); or
  (b) is a group of the formula VI $$\text{(VI)}$$

[structure: benzene ring with H at four positions and OY² substituent]

and $Y^2$ is pyridyl, pyrimidinyl, triazinyl and benzoxazolyl and is optionally substituted by one or more, preferably up to three, identical or different radicals selected from the group consisting of fluorine, chlorine, trifluoromethyl, methyl and/or methoxy.

The present invention also relates to the corresponding pyridine-N-oxides of the compounds of the formula I. They are obtained by oxidizing the compounds of the formula I with hydrogen peroxide or with a peracid, such as perbenzoic acid, peracetic acid, monoperphthalic acid or Caro's acid.

The present invention relates to the compounds of the formula I in the form of the free base or of an acid addition salt. Acids which can be used for salt formation are inorganic acids, such as hydrochloric acid, hydrobromic acid, nitric acid, sulfuric acid, phosphoric acid, or organic acids, such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

Some of the compounds of the formula I have one or more asymmetric carbon atoms. Racemates and diastereomers may therefore occur. The invention embraces the pure isomers and also their mixtures. The mixtures of diastereomers can be resolved into the components by customary methods, for example by selective crystallization from suitable solvents, or by chromatography. Racemates can be resolved into the enantiomers by customary methods, for example by a salt formation with an optically active acid, separation of diastereomeric salts and liberation of the pure enantiomers by means of a base.

The N-(4-pyridyl)carboxamides of the formula I can be prepared by standard methods from 4-aminopyridines of the formula VIII in which A, $R^1$, $R^2$, $R^3$ and $R^4$ are as defined above and carboxylic acids or their derivatives of the formula IX in which Y and Z are as defined above and L is a leaving group, preferably hydroxyl or chlorine [for example: Methoden der Organischen Chemie/Houben-Weyl [Methods in Organic Chemistry] (J. Falbe, Ed.), 4th Edition, Vol. E5, Part 2, Pages 934–1135, Thieme, Stuttgart 1985].

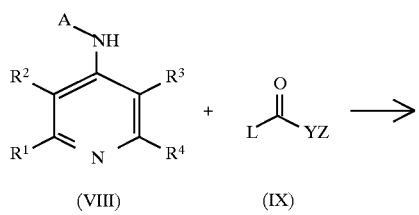

The abovementioned reaction is carried out in a temperature range between 10° C. and the boiling point of the reaction mixture, if appropriate in an inert organic solvent, such as dichloromethane, toluene, chlorobenzene or xylene. Mixtures of the abovementioned solvents can also be used.

Compounds of the formula IX are commercially available or can be obtained by processes known in principle [for example: Indian J. Chem. 24, 71 (1985); J. Chem Soc. 4299 (1954); J. Chem Soc. Perkin Trans. 1, 2763 (1991); J. Org. Chem. 11, 798 (1946); J. Med. Chem. 22, 1068 (1979); J. Chem. Soc. Perkin Trans. 1, 1926 (1987); Synthesis 63 (1991); Tetrahedron 45, 5895 (1989)].

Compounds of the formula VIII in which A is hydrogen and $R^1$, $R^2$, $R^3$ and $R^4$ are as defined above under (1) are novel in some cases and also provided by the invention.

Preferred compounds of the formula VIII are those in which $R^1$ and $R^2$ are identical or different and independently of one another are halocyclopropyl, ($C_1$–$C_2$) alkoxymethyl, halomethoxymethyl, halomethoxyhalomethyl, methoxyhalomethyl or cyano; or only one of the radicals $R^1$ and $R^2$ is as defined above and the other radical is halogen, ($C_1$–$C_4$)alkyl, halo($C_1$–$C_2$) alkyl, cyclopropyl, methoxy or ethoxy; and A, $R^3$ and $R^4$ in each case are hydrogen;

in particular those compounds in which $R^1$ is methoxymethyl;

$R^2$ is halogen, cyano or methoxy and

A, $R^3$ and $R^4$ are in each case hydrogen.

Some of the compounds of the formula VIII can be prepared by methods known in principle [for example: J. Med. Chem. 32, 1970 (1989); J. Prakt. Chem. 331, 369 (1989); J. Prakt. Chem. 327, 521 (1985); J. Gen. Chem. USSR (1959), 898].

In some cases, the abovementioned methods for the preparation of compounds of the formula VIII are suitable to a limited extent only, or not at all. In these cases, a novel process was used, which was also provided by the invention and will be described hereinbelow.

The invention therefore furthermore relates to a process for the preparation of compounds of the formula VIII, which comprises subjecting compounds of the formula X in which $R^1$, $R^2$, $R^3$ and $R^4$ are as defined above and R' is a substituent on the benzyl to a reductive conversion by known methods R. Huisgen et al., Chem. Ber. 101, 2559 (1968); C. H. Rayburn, W. R. Harlan, H. R. Hammer, J. Am. Soc. 72, 1721 (1950)] to give the compounds of the formula VIII.

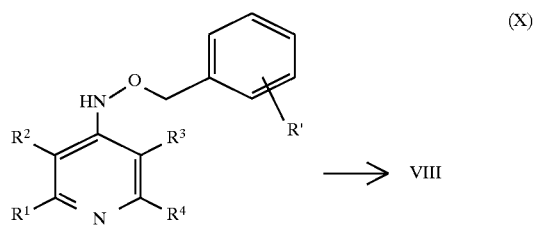

Compounds of the formula X have already been proposed (German Patent Applications P 43 31 181.4, P 43 31 179.2, P 43 31 180.6).

The compounds of the formula I according to the invention are distinguished by an outstanding fungicidal action. Fungal pathogens which have already penetrated the plant tissue can be successfully controlled curatively. This is particularly important and advantageous in the case of those fungal diseases which, once infection has taken place, can no longer be controlled effectively with the fungicides which are otherwise customary. The spectrum of action of the claimed compounds embraces a variety of economically important phytopathogenic fungi, such as, for example, *Phytophthora infestans, Plasmopara viticola*, but also *Erysiphe graminis* and Pyrenophora.

In addition, the compounds according to the invention are also suitable for use in technical fields, for example as wood preservatives, as preservatives, in sealing compositions, in paints, in cooling lubricants for metal working, or as preservatives in drilling and cutting oils.

The active substances according to the invention in their commercially available formulations can be employed either on their own or in combination with other fungicides known from the literature.

Examples of fungicides which are known from the literature and which can be combined according to the invention with the compounds of the formula I are, for example, the following products: aldimorph, andoprim, anilazine, BAS 480F, BAS 490F, benalaxyl, benodanil, benomyl, binapacryl, bitertanol, bromuconazole, buthiobate, captafol, captan, carbendazim, carboxin, CGA 173506, chlobenzthiazone, chlorthalonil, cymoxanil, cyproconazole, cyprofuram, dichlofluanid, dichlomezin, diclobutrazol, diethofencarb, difenconazole (CGA 169374), difluconazole, dimethirimol, dimethomorph, diniconazole, dinocap, dithianon, dodemorph, dodine, edifenfos, ethirimol, etridiazole, fenarimol, fenfuram, fenpiclonil, fenpropidin, fenpropimorph, fentin acetate, fentin hydroxide, ferimzone (TF164), fluazinam, fluobenzimine, fluquinconazole, fluorimide, flusilazole, flutolanil, flutriafol, folpet, fosetyl-aluminum, fuberidazole, fulsulfamide (MT-F651), furalaxyl, furconazole, furmecyclox, guazatine, hexaconazole, ICI ASS 04, imazalil, imiben-conazole, iprobenfos, iprodione, isoprothiolane, KNF 317, copper compounds, such as copper oxychloride, oxine-copper, copper oxides, mancozeb, maneb, mepanipyrim (KIF 3535), metconazole mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyroquilon, rabenzazole, RH7592, sulfur, tebuconazole, TF 167, thiabendazole, thicyofen, thiofanate-methyl, thiram, tolclofos-methyl, tolylfluanid, triadimefon, triadimenol, tricyclazole, tridemorph, triflumizol, triforine, validamycin, vinchlozolin, XRD 563, zineb, sodium dodecylsulfonate, sodium dodecyl sulfate, sodium C13/C15-alcohol ether sulfonate, sodium cetostearyl phosphate ester, dioctyl sodium sulfosuccinate, sodium isopropylnaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quaternized fatty amines, alkyldimethylbenzylammonium chloride and 1-hydroxyethyl-2-alkylimidazoline.

The abovementioned components for combinations are known active substances, most of which are described in CH. R. Worthing, U. S. B. Walker, The Pesticide Manual, 7th Edition (1983), British Crop Protection Council.

Being well tolerated by plants and having a favorable toxicity to warm-blooded species, the active substances are furthermore suitable for controlling animal pests, in particular insects, arachnids, nematodes, Helminthes and mollusks, very particularly preferably for controlling insects, nematodes and arachnids found in agriculture, livestock breeding, in forests, in the protection of stored products and materials, and in the hygiene sector. They are active against normally sensitive and resistant species and against all or some stages of development.

The abovementioned pests include:

From the order of the Acarina, for example, *Acarus siro, Agras spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp., Eotetranychus spp., Oligonychus spp.* and *Eutetranychus spp.*

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spp.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria.*

From the order of the Isoptera, for example, *Reticulitermes spp.*

From the order of the Anoplura, for example, *Phylloxera vastatrix, Pemphigus spp., Pediculus humanus corporis, Haematopinus spp.* and *Linognathus spp.*

From the order of the Mallophaga, for example, *Trichodectes spp.* and *Damalinea spp.*

From the order of the Thysanoptera, for example, *Hercinothrips femoralis* and *Thrips tabaci.*

From the order of the Heteroptera, for example, *Eurygaster spp., Dysdercus intermedius, Piesma quadrata, Cimex lectularius, Rhodnius prolixus* and *Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelus bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp.*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylloides chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica.*

From the order of the Hymenoptera, for example, *Diprion spp., Hoplocampa spp., Lasius spp., Monomorium pharaonis* and *Vespa spp.*

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hypobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphonaptera, for example, *Xenopsylla cheopis* and *Ceratophyllus spp.*

From the order of the Arachnida, for example, *Scorpio maurus* and *Latrodectus mactans.*

From the class of the Helminthes, for example, Haemonchus, Trichostrongulus, Ostertagia, Cooperia, Chabertia, Strongyloides, Oesophagostomum, Hyostrongulus, Ancylostoma, Ascaris and Heterakis and Fasciola and plant-pathogenic nematodes, for example those of the genera Meloidogyne, Heterodera, Ditylenchus, Aphelenchoides, Radopholus, Globodera, Pratylenchus, Longidorus and Xiphinema.

From the class of the Gastropoda, for example, *Deroceras spp., Arion spp., Lymnaea spp., Galba spp., Succinea spp., Biomphalaria spp., Bulinus spp., Oncomelania spp.,*

From the class of the Bivalva, for example, *dreissena spp.*

The plant-parasitic nematodes which can be controlled according to the invention include, for example, the root-parasitic soil-dwelling nematodes, such as, for example, those from the genera Meloidogyne (such as root-knot eelworms, such as *Meloidogyne incognita, Meloidogyne hapla* and *Meloidogyne javanica*), Heterodera and Globodera (cyst nematodes, such as *Globodera rostochiensis, Globodera pallida, Heterodera trifolii*) and of the genera Radopholus, such as *Radopholus similis*, Pratylenchus, such as *Pratylenchus neglectus, Pratylenchus penetrans* and *Pratylenchus curvitatus;*

Tylenchulus, such as *Tylenchulus semipenetrans,* Tylenchorhynchus, such as *Tylenchorhynchus dubius* and *Tylenchorhynchus claytoni*, Rotylenchus, such as *Rotylenchus robustus*, Heliocotylenchus, such as *Haliocotylenchus multicinctus*, Belonoaimus, such as *Belonoaimus longicaudatus*, Longidorus, such as *Longidorus elongatus*, Trichodorus, such as *Trichodorus primitivus* and Xiphinema, such as *Xiphinema index.*

Furthermore, the compounds according to the invention can be used for controlling the nematode genera Ditylenchus (stem parasites, such as *Ditylenchus dipsaci* and *Ditylenchus destructor*), Aphelenchoides (foliar nematodes, such as *Aphelenchoides ritzemabosi*) and Anguina (seed-gall nematodes, such as *Anguina tritici*).

The invention also relates to compositions which comprise the compounds of the formula I in addition to suitable formulation auxiliaries.

The compositions according to the invention generally comprise 1 to 95% by weight of the active substances of the formula I.

They can be formulated in various ways, depending on the biological and/or chemico-physical parameters which prevail. The following are therefore suitable possibilities for formulations:

wettable powders (WP) emulsifiable concentrates (EC), aqeuous solutions (SC), emulsions, sprayable solutions, oil- or water-based dispersions (SC), suspoemulsions (SC), dusts (SC), seed-treatment products, granules in the form of microgranules, spray granules, coated granules and adsorption granules, waterdispersible granules (WG), ULV formulations, microcapsules, waxes or baits.

These individual types of formulations are known in principle and are described, for example, in Winnacker-Küchler, "Chemische Technologie" [Chemical Technology], Volume 7, C. Hauser Verlag Munich, 4th Edition 1986; van Falkenberg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N.J.; H. V. Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte", [Surface-active Ethylene Oxide Adducts], Wiss. Verlagsgesell; Stuttgart 1976; and Winnacker-Küchler, "Chemische Technologie" [Chemical Technology], Volume 7, C. Hauser Verlag Munich, 4th Edition 1986.

Based on these formulations, it is also possible to prepare combinations with other pesticidally active substances, fertilizers and/or growth regulators, for example in the form of a ready mix or a tank mix. Wettable powders are preparations which are uniformly dispersible in water and which, besides the active substance, additionally comprise wetting agents, for example polyethoxylated alkylphenols, polyethoxylated fatty alcohols, alkylsulfonates or alkylphenolsulfonates and dispersants, for example sodium lignosulfonate, sodium 2,2'-binaphthylmethane-6,6'-disulfonate, sodium dibutylnaphthalenesulfonate, or else sodium oleylmethyltauride, in addition to a diluent or inert substance. Emulsifiable concentrates are prepared by dissolving the active substance in an organic solvent, for example butanol, cyclohexanone, dimethylformamide, xylene or else higher-boiling aromatics or hydrocarbons, with the addition of one or more emulsifiers. Examples of emulsifiers which can be used are: calcium alkylarylsulfonates, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusts are obtained by grinding the active substance with finely divided solid substances, for example talc, natural clays, such as kaolin, bentonite, pyrophillite, or diatomaceous earth. Granules can be prepared either by spraying the active substance onto adsorptive, granulated inert material or by applying active substance concentrates to the surface of carriers, such as sand, kaolinites or granulated inert material, with the aid of binders, for example polyvinyl alcohol, sodium polyacrylate or else mineral oils. Suitable active substances can also be granulated in the manner which is customary for the preparation of fertilizer granules, if desired in the form of a mixture with fertilizers.

The active substance concentration in wettable powders is for example approximately 10 to 90% by weight, the remainder to 100% by weight being composed of customary formulation components. In the case of emulsifiable concentrates, the active substance concentration can amount to approximately 5 to 80% by weight. Formulations in the form of dusts usually comprise 5 to 20% by weight of active substance, sprayable solutions approximately 2 to 20% by weight. In the case of granules, the active substance content partly depends on whether the active compound is in liquid or solid form and on which granulation auxiliaries, fillers and the like are being used.

In addition, the abovementioned formulations of active substance optionally comprise the adhesives, wetting agents, dispersants, emulsifiers, penetrants, solvents, fillers or carriers which are customary in each case.

For use, the concentrations, which are in commercially available form, are optionally diluted in the customary manner, for example using water in the case of wettable powders, emulsifiable concentrates, dispersions and, in some cases also microgranules. Dusts and granulated preparations and also sprayable solutions are conventionally not diluted further with other inert substances prior to use.

The application rate required varies, depending on the external conditions such as, inter alia, temperature and humidity. It can vary within wide limits, for example between 0.001 and 10.0 kg/ha or more of active substance, but it is preferably between 0.005 and 5 kg/ha.

The active substances according to the invention, in their commercially available formulations and in the use forms which are prepared with these formulations, can exist as a mixture with other active substances, such as insecticides, attractants, sterilants, acaricides, nematicides, fungicides, growth-regulating substances or herbicides.

The pesticides include, for example, phosphoric esters, carbamates, carboxylic esters, formamidines, tin compounds, substances produced by microorganisms, and the like. Preferred components for the mixtures are 1. from the group of the phosphorus compounds, acephate, azamethiphos, azinphos-ethyl, azinphosmethyl, bromophos, bromophos-ethyl, chlorfenvinphos, chlormephos, chlorpyrifos, chlorpyrifos-methyl, demeton, demeton-S-methyl, demeton-S-methylsulfon, dialifos, diazinon, dichlorvos, dicrotophos, O,O-1,2,2,2-tetrachloroethyl phosphorothioate (SD 208 304), dimethoate, disulfoton, EPN, ethion, ethoprophos, etrimfos, famphur, fenamiphos, fenitrothion, fensulfothion, fenthion, fonofos, formothion, heptenophos, isazophos, isothioate, isoxathion, malathion, methacrifos, methamidophos, methidathion, salithion, mevinphos, monocrotophos, naled, omethoate, oxydemeton-methyl, parathion, parathionmethyl, phenthoate, phorate, phosalone, phosfolan, phosmet, phosphamidon, phoxim, pirimiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon, vamidothion;

2. from the group of the carbamates, aldicarb, 2-sec-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenyl butyryl(methyl)carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio-(ethylideneamino)-N-methyl-N-(morpholinothio) carbamate (UC 51717);

3. from the group of the carboxylic esters allethrin, alphametrin, 5-benzyl-3-furylmethyl (E)-(1R)cis-2,2-dimethyl-3-(2-oxothiolan-3-ylidenemethyl)cyclopropanecarboxylate, bioallethrin, bioallethrin ((S)-cyclopentyl isomer), bioresmethrin, biphenate, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, pheothrin ((R) isomer), d-pralethrin, pyrethrine (natural products), resmethrin, tefluthrin, tetramethrin, tralomethrin;

4. from the group of the amidines, amitraz, chlordimeform;

5. from the group of the tin compounds, cyhexatin, fenbutatin oxide;

6. Others abamectin, Bacillus thuringiensis, bensultap, binapacryl, bromopropylate, buprofezin, camphechlor, cartap, chlorobenzilate, chlorofluazuron, 2-(4-chlorophenyl)-4,5-diphenylthiophene (UBI-T 930), chlorfentezine, 2-naphthylmethyl cyclopropanecarboxylate (Ro12-0470), cyromazin, ethyl N-(3,5-dichloro-4-(1,1,2,3,3,3-hexafluoro-1-propyloxy)phenylcarbamoyl)-2-chlorobenzocarboximidate, DDT, dicofol, N-(N-(3,5-dichloro-4-(1,1,2,2-tetrafluoroethoxy)phenylamino) carbonyl)-2,6-diflurobenzamide (XRD 473), diflubenzuron, N-(2,3-dihydro-3-methyl-1,3-thiazol-2-ylidene)-2,4-xylidine, dinobuton, dinocap, endosulfan, ethofenprox, (4-ethoxyphenyl) (dimethyl) (3-(3-phenoxyphenyl)propyl)silane, (4-ethoxyphenyl) (3-(4-fluoro-3-phenoxyphenyl)propyl)dimethylsilane, fenoxycarb, 2-fluoro-5-(4-(4-ethoxyphenyl)-4-methyl-1-pentyl)diphenyl ether (MTI 800), granuloses and nuclear polyhedrosis viruses, fenthiocarb, flubenzimine, flucycloxuron, flufenoxuron gamma-HCH, hexythiazox, hydramethylnon (AC 217300), ivermectin, 2-nitromethyl-4,5-dihydro-6H-thiazine (SD 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, triflumuron.

The active substance content of the use forms prepared from the commercially available formulations can be between 0.00000001 and 95% by weight of active substance, preferably between 0.00001 and 1% by weight.

They are used in a manner adapted to suit the use forms.

The active substances according to the invention are also suitable for controlling endo- and ectoparasites in the field of veterinary medicine or in the field of animal keeping.

Here, the active substances according to the invention are used in a known manner, such as by oral administration, for example in the form of tablets, capsules, drinks, or granules, or by dermal administration, for example in the form of dipping, spraying, pouring-on, spotting-on and dusting, and also by parenteral administration, for example in the form of an injection.

Accordingly, the novel compounds of the formula I according to the invention can also be employed particularly advantageously in livestock keeping (for example cattle, sheep, pigs and poultry, such as chickens, geese and the like). In a preferred embodiment of the invention, the novel compounds, if appropriate in the form of suitable formulations (cf. above), are administered to the animals orally, if appropriate together with the drinking water or the feed. Since they are effectively excreted with the feces, the development of insects in the animal's feces can thus be prevented very easily. The doses and formulations which are suitable in each case depend, in particular, on the species and the development stage of the livestock and also on the danger of infestation, and can readily be determined and decided by the customary methods. For example, the novel compounds can be employed in cattle at doses from 0.01 to 1 mg/kg of bodyweight.

The examples which follow are intended to illustrate the invention without imposing any limitation.

A. FORMULATION EXAMPLES a) A dust is obtained by mixing 10 parts by weight of active substance and 90 parts by weight of talc as inert substance and comminuting the mixture in a hammer mill.

b) A wettable powder which is readily dispersible in water is obtained by mixing 25 parts by weight of active substance, 65 parts by weight of kaolin-containing quartz as inert substance, 10 parts by weight of potassium lignosulfonate and 1 part by weight of sodium oleoylmethyltaurate as wetting agent and dispersant and grinding the mixture in a pinned-disk mill.

c) A dispersion concentrate which is readily dispersible in water is prepared by mixing 40 parts by weight of active substance with 7 parts by weight of a sulfosuccinic monoester, 2 parts by weight of a sodium lignosulfonate and 51 parts by weight of water, and grinding the mixture in a ball mill to a fineness of below 5 microns.

d) An emulsifiable concentrate can be prepared from 15 parts by weight of active substance, 75 parts by weight of cyclohexanone as the solvent and 10 parts by weight of ethoxylated nonylphenyl (10 EO) as the emulsifier.

e) Granules can be prepared from 2 to 15 parts by weight of active substance and an inert granule carrier, such as attapulgite, pumice granules and/or quartz sand. It is expedient to use a suspension of the wettable powder of Example b) with a solids content of 30%, spraying this suspension onto the surface of attapulgite granules, and drying and mixing this intimately. Here, the wettable powder amounts to approximately 5% by weight and the inert carrier to approximately 95% by weight of the finished granules.

B. BIOLOGICAL EXAMPLES

Example 1
Activity against two-spotted spider mites

Bean plants (*Phaseolus vulgaris ssp. vulgaris* var. *nanus*) which were severely infested with the two-spotted spider mite (*Tetranychus urticae*, full population) were sprayed to run off point with an aqueous preparation comprising 250 ppm of the active substance in question. After the plants have been grown in the greenhouse for 7 days, the mortality of the spider mites (full population) was checked. A mortality of 100% was found in the case of the following examples:

1, 2, 14, 131, 154

Example 2
Activity against the fruit tree red spider mite

Apple plants (*Malus domestica*) which were severely infested with the fruit tree red spider mites (*Panonychus ulmi*, full population) were sprayed to run off point with an aqueous preparation comprising 250 ppm of the active substance in question. After the plants were grown in the greenhouse for 9 days, the mortality of the fruit tree red spider mites (full population) was checked. A mortality of 100% was found in the case of the following examples:

1, 2, 14, 131, 154

Example 3
Activity against the black bean aphid

Field bean plants (*Vicia faba*) which were severely populated with black bean aphids (*Aphis fabae*, full population) were sprayed to run off point with an aqueous preparation comprising 250 ppm of the active substance in question. After the plants had been grown in the greenhouse for 3 days, the mortality of the aphids (full population) was checked. A mortality of 100% was found in the case of the following examples:

1, 2, 14, 131, 154, 259

Example 4
Activity against eggs of the large milkweed bug eggs

Filter paper disks supporting eggs (age of the eggs: 2 days) of the large milkweed bug were treated with 1 ml aliquots of an aqueous preparation comprising 250 ppm of the active substance in question. After the coating had dried on, the filter paper disks were stored in Petri dishes at room temperature at maximum atmospheric humidity. After 7 days, the ovicidal activity was determined. An ovicidal activity of 100% (egg mortality) was found in the case of the following examples:

2, 14, 78

Example 5
Activity against whitefly

Bean plants (*Phaseolus vulgaris ssp. vulgaris* var. *nanus*) which were severely populated with whiteflies (*Trialeurodes vaporariorum*, 3-day old eggs) were sprayed to run off point with an aqueous preparation comprising 250 ppm of the active substance in question. After the plants had been grown in the greenhouse for 14 days, the mortality of the whiteflies (full population) was checked. A mortality of 100% was found in the case of the following examples:

1, 2, 3, 14, 131, 154

Example 6
Activity against the citrus mealybuq

Bean plants (*Phaseolus vulgaris ssp. vulgaris* var. *nanus*) which were severely infested with the citrus mealybug (*Planococcus citri*, 2nd instar larvae) were sprayed to run off point with an aqueous preparation comprising 250 ppm of the active substance in question. After the plants had been grown in the greenhouse for 7 days, the mortality of the citrus mealybugs (full population) was checked. A mortality of 100% was found in the following examples:

2, 14

Example 7
*Musca domestica* (common housefly)

The bottom and lid of a Petri dish are coated on the inside with in each case 3 ml of an aqueous dilution of a wettable powder concentrate comprising 250 ppm of the active substance in question. After the coating had dried on, the Petri dishes were populated with 24-hour old common houseflies (*Musca domestica*) and covered with the treated lid. After 3 hours at room temperature 20° C., the mortality of the flies was checked. A destruction rate of 100% was achieved with the compound of Examples 14 and 259.

Example 8
*Diabrotica undecimpunctata*

Filter paper disks were treated with 1 ml aliquots of the aqueous dilution of a wettable powder concentrate comprising 250 ppm of the active substance in question nd stored in the open until they had dried. Thereupon, the filter paper was placed on the bottom of a Petri dish and 1 ml aliquots of (distilled) water were applied dropwise. 10 larvae (L3) of *Diabrotica undecimpunctata* were subsequently placed on the filter paper, and the Petri dish was closed and stored in the dark at 28° C. for 48 hours. Thereupon, the mortality of the larvae was determined. A destruction rate of 100% was achieved with the compounds of Examples 1, 2, 3, 14, 78, 131, 154, 258 and 259.

Example 9
*Nilaparvarta lugens*

Rice seed was germinated under moist conditions and sprouted in dishes until the plantlets were approximately 10 cm high. Batches of 3 rice plants were planted into glass tubes which had been filled with wet cotton wool, and the leaves of the rice plants were immersed into an aqueous dilution of a wettable powder concentrate comprising 250 ppm of the active substance in question. After the coating had dried on, the plants together with the tubes were placed on the bottom of a dish, batches of 10 specimens of the brown planthopper (*Nilaparvata lugens*, L3) were introduced into the dish, and the dish was sealed and stored at 25° C. The mortality of the planthoppers was checked after 3 days. A mortality rate of 100% was achieved with the compounds of Examples 1, 14 and 131.

Example 10
Ovicidal activity (*Manduca sexta*)

The inside of Petri dish bottoms was covered with Japan filter paper, and batches of 20 1-day old eggs of *Manduca sexta* were placed on the paper. Then, approximately 1 ml of an artificial insect feed diet was placed in the middle of the Petri dish, and the inside of the bottom, together with eggs and feed diet, was sprayed with an aqueous wettable powder suspension of the test products (250 ppm) corresponding to a rate of 600 l/ha. After the Petri dish had been sealed and stored at room temperature for 5 days, the mortality of the eggs was determined. The compounds of Examples 2 and 14 resulted in an activity of 100%.

Example 11

*Spodoptera littoralis*

Larvae (L3) of the butterfly species *Spodoptera littoralis* were placed into Petri dishes containing approximately 5 ml of an artificial feed diet and sprayed with aqueous dilutions of a wettable powder suspension of the test compounds (250 ppm) at an application rate corresponding to 600 l/ha. Thereupon, the Petri dishes were sealed and stored at room temperature for 5 days. Thereupon, the mortality of the animals which had been introduced was determined. The compounds of Examples 1, 14 and 131 resulted in an activity of 100%.

Example 12

Control of root-knot eelworms

An aqueous preparation comprising 0.03% of active substance is prepared in a glass container (end volume 30 ml). To this batch there are added approximately 5000 freshly-hatched, active, mobile, larvae (2nd development stage) of root-knot eelworms (*Meloidogyne incognita*). After the nematode larvae had been exposed continuously for 48 hours, the percentage of the individuals which had become immobile due to exposure to the active substance was determined in comparison with the untreated controls. This percentage is termed nematicidal contact action in percent (part A of the test).

After this part of the test has been concluded, the entire solution (active substance and pretreated nematode larvae) is poured into a pot containing five precultured cucumber plants (*Cucumis sativus*) (soil volume 100 ml; age of the cucumber plants: 7 days after sowing). This drench application reduces the active substance content to 0.009% relative to the soil volume. The host plants which have been treated in this manner are subsequently grown on in the greenhouse (25° to 27° C., watering twice daily). After two weeks, the host plants together with the root balls are removed from the eelworm-infested soil mixture and freed from adhering soil. Plant growth and root formation of the host plants are assessed visually and the results recorded. The root knots per plant are subsequently counted and the number compared with the infestation of untreated control plants. The reduced infestation in percent, as the criterion for assessing the activity, is calculated using Abbott's formula. The result is termed nematicidal soil drench action in percent (part B of the test).

In parts A and B of the test, the compounds of Examples 1, 14, 131, 3 and 78 showed an activity against the root-knot eelworm Meloidogyne incognita of 90 to 100%.

C. CHEMICAL EXAMPLES

Example 1

N-(3-chloro-2-methoxymethyl-4-pyridinyl)-2-[4-(4-chloro-phenoxy)-phenyl]-acetamide:

0.58 g (3.36 mmol) of 4-amino-3-chloro-2-methoxymethylpyridine was added to 0.94 g (3.36 mmol) of 4-(4-chloro-phenoxy)phenylacetyl chloride in 40 ml of xylene, and the mixture was refluxed for 8 hours. After the xylene had been removed in vacuo, the residue was taken up in methylene chloride. The mixture was washed with water and 0.1N aqueous sodium hydroxide solution, the combined aqueous phases were rendered neutral and extracted three times using ethyl acetate, and the ethyl acetate phase was dried over sodium sulfate. After the solvent had been removed in vacuo and the residue purified by column chromatography (silica gel, ethyl acetate:petroleum ether= 80:20), 0.40 g of a yellow oil were obtained.

$^1$H NMR (CDCl$_3$): δ=3.45 (s,3H), 3.80 (s,2H), 4.62 (s,2H), 6.95 (d,2H), 7.05 (d,2H), 7.32 (m,4H), 7.95 (s,1H), 8.35 (d,1H), 8.45 (d,1H).

Example 2

2-(4-Benzyloxy-phenyl)-N-(3-methoxy-2-methoxymethyl-4-pyridinyl)-acetamide:

10.0 g (5.95 mmol) of 4-amino-2-methoxy-3-methoxymethyl-pyridine were added to 1.55 g (5.95 mmol) of 4-benzyl-oxyphenylacetyl chloride in 60 ml of xylene, and the mixture was refluxed for 8 hours. After the xylene had been removed in vacuo, the residue was taken up in methylene chloride. It was washed with water, 0.1N aqueous sodium hydroxide solution, and saturated aqeuous sodium chloride solution, the combined aqueous phases were rendered neutral and extracted three times with ethyl acetate, and the ethyl acetate phase was dried over sodium sulfate. After the solvent had been removed in vacuo and the residue purified by column chromatography (silica gel, ethyl acetate), 0.40 g of a yellowish brown oil were obtained.

$^1$H NMR (CDCl$_3$): δ=3.40 (s,3H) , 3.44 (s,3H) , 3.72 (s,2H) , 4.50 (s,2H), 5.12 (s,2H), 7.05 (d,1H), 7.36 (m,7H), 7.88 (s,1H), 8.27 (m,2H).

The compounds of the table which follows were obtained analogously to Examples 1 and 2.

TABLE 1

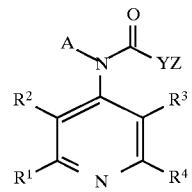

| No. | A | R$^1$ | R$^2$ | R$^3$ | R$^4$ | Y—Z | Physical properties |
|---|---|---|---|---|---|---|---|
| 3 | H | —CH$_2$OCH$_3$ | —OCH$_3$ | H | H | 4-fluorobenzyl | $^1$H NMR(CDCl$_3$): δ= 3.42(s, 3H), 3.54 (s, 3H), 3.79 (s, 2H), 4.51(s, 2H), 7.88 (s, 1H) |

TABLE 1-continued

| No. | A | R¹ | R² | R³ | R⁴ | Y—Z | Physical properties |
|---|---|---|---|---|---|---|---|
| 4 | H | —CH₂CH₃ | I | H | H | 4-trifluoromethyl-benzyl | |
| 5 | H | —CH₂CH₃ | I | H | H | 4-(4-chloro-phenoxy)-benzyl | |
| 6 | H | —CH₂CH₃ | I | H | H | 4-(4-chloro-phenoxy)-phenoxymethyl | |
| 7 | H | —CH₂CH₃ | I | H | H | 2-(4-(4-chloro-phonoxy)-phenoxy)-ethyl | |
| 8 | H | —CH₂CH₃ | I | H | H | cis-4-methyl-cyclo-hexyl | |
| 9 | H | CH₂CH₃ | CN | H | H | cis-4-methylcyclo-hexyl | |
| 10 | H | —CH₂CH₃ | CN | H | H | 4-(4-chloro-phenoxy)-benzyl | |
| 11 | H | —CH₂CH₃ | CN | H | H | 4-(4-cyano-phenoxy)-benzyl | |
| 12 | H | —CH₂CH₃ | CN | H | H | 4-(4-nitro-phenoxy)-benzyl | |
| 13 | H | —CH₂OCH₃ | H | H | H | 4-(4-chloro-phenoxy)-benzyl | |
| 14 | H | —CH₂OCH₃ | —OCH₃ | H | H | 4-(4-chloro-phenoxy)-benzyl | ¹H NMR(CDCl₃): δ= 3.45(s, 3H), 3.59 (s, 2H), 3.80(s, 2H), 4.53(s, 2H), 6.95 (d, 2H), 7.05(d, 2H), 7.32(m, 4H), 7.92 (s, 1H), 8.30(m, 2H). |
| 15 | H | —CH₂OCH₃ | —OCH₃ | H | H | 4-butoxy-benzyl | |
| 16 | H | —CH₂OCH₃ | —OCH₃ | H | H | 4-ethoxy-benzyl | |
| 17 | H | —CH₂OCH₃ | —OCH₃ | H | H | 4-methoxybenzyl | |
| 18 | H | —CH₂OCH₃ | —OCH₃ | H | H | 4-trifluoromethyl-benzyl | |
| 19 | H | —CH₂OCH₃ | —OCH₃ | H | H | naphthalen-1-ylmethyl | |
| 20 | H | CH₂OCH₃ | Cl | H | H | biphenylyl-4-ylmethyl | |
| 21 | H | —CH₂OCH₃ | Cl | H | H | 4-benzyloxy-benzyl | |
| 22 | H | —CH₂OCH₃ | Cl | H | H | 4-(4-nitro-phenoxy)-benzyl | |
| 23 | H | —CH₂OCH₃ | Cl | H | H | 4-(4,6-dimethyl-pyrimidin-2-yloxy)-benzyl | |
| 24 | H | —CH₂OCH₃ | Cl | H | H | 4-(4-methoxy-6-methyl-[1,3,5]triazin-2-yloxy)-benzyl | |
| 25 | H | —CH₂OCH₃ | CN | H | H | 4-(4-chloro-phenoxy)-benzyl | |
| 26 | H | —CH₂OCH₃ | CN | H | H | 4-(4,6-dimethoxy-[1,3,5]triazin-2-yloxy)-benzyl | |
| 27 | H | —CH₂OCH₃ | CN | H | H | 4-phenoxy-benzyl | |
| 28 | H | —CH₂OCH₃ | Br | H | H | 4-(4-chloro-phenoxy)-benzyl | |
| 29 | H | —CH₂OCH₃ | Br | H | H | 4-(4-cyano-phenoxy)-benzyl | |
| 30 | H | —CH₂OCH₃ | Br | H | H | 4-butoxy-benzyl | |
| 31 | H | —CH₂OCH₃ | Br | H | H | 4-trifluoromethyl-benzyl | |
| 32 | H | —CH₂OCH₃ | CN | H | H | 4-(2,3,4,5,6-pentafluorophenoxy)-benzyl | |
| 33 | H | —CH₂OCH₃ | —OCH₃ | H | H | 4-(4-chloro-phenoxy)-phenoxymethyl | |
| 34 | H | —CH₂OCH₃ | —OCH₃ | H | H | 4-(4-cyano-phenoxy)-phenoxymethyl | |
| 35 | H | —CH₂OCH₃ | —OCH₃ | H | H | 4-(2,3,4,5,6-pentafluorophenoxy)-phenoxymethyl | |

TABLE 1-continued

| No. | A | R¹ | R² | R³ | R⁴ | Y—Z | Physical properties |
|---|---|---|---|---|---|---|---|
| 36 | H | —CH₂OCH₃ | —OCH₃ | H | H | 4-(4,6-dimethoxy-pyrimidin-2-yloxy)-benzyl | |
| 37 | H | —CH₂OCH₃ | —OCH₃ | H | H | 4-(4-methoxy-6-methyl-pyrimidin-2-yloxy)-benzyl | |
| 38 | H | —CH₂OCH₃ | —OCH₃ | H | H | 4-(4,6-di-methoxy[1,3,5]tria-zin-2-yloxy)-benzyl | |
| 39 | H | —CH₂OCH₃ | OCH₃ | H | H | 4-(2,3,4,5,6-penta-fluorophenoxy)-phenoxymethyl | |
| 40 | H | —CH₂OCH₃ | OCH₃ | H | H | cis-4-(4-chloro-phenyl)-cyclohexyl | |
| 41 | H | —CH₂OCH₃ | OCH₃ | H | H | cis-H-tert-butyl-cyclohexyl | |
| 42 | H | —CH₂OCH₃ | OCH₃ | H | H | 4-(6-chloro-ben-zoxazol-2-yloxy)-benzyl | |
| 43 | H | —CH₂OCH₃ | OCH₃ | H | H | 2-[4-(4-chloro-phenoxy)-phenoxy]-ethyl | |
| 44 | H | —CH₂OCH₃ | OCH₃ | H | H | 2-(4-cyclopentyl-phenoxy)-ethyl | |
| 45 | H | —CH₂OCH₃ | OCH₃ | H | H | 4-cyclopentyl-benzyl | |
| 46 | H | —CH₂OCH₃ | OCH₃ | H | H | 4-tert-butyl-benzyl | |
| 47 | H | —CH₂OCH₃ | OCH₃ | H | H | 4-chloro-phenyl | |
| 48 | H | —CH₂OCH₃ | OCH₃ | H | H | (4-chloro-phenoxy)-phenyl | |
| 49 | H | —CH₂OCH₃ | OCH₃ | H | H | 4-(4,6-diisopropyl-pyrimidin-2-yloxy)-benzyl | |
| 50 | H | —CH₂OCH₃ | OCH₃ | H | H | 4-trifluoromethoxy-benzyl | |
| 51 | H | —CH₂OCH₃ | OCH₃ | H | H | 7-bromo-heptyl | |
| 52 | H | —CH₂OCH₃ | OCH₃ | H | H | 2-cyclopentyl-ethyl | |
| 53 | H | —CH₂OCH₃ | OCH₃ | H | H | n-pentadecyl | |
| 54 | H | —CH₂OCH₃ | OCH₃ | H | H | 4-tert-butyl-phenyl | |
| 55 | H | —CH₂OCH₃ | OCH₃ | H | H | 4-(pyridin-4-yloxy)-benzyl | |
| 56 | H | —CH₂OCH₃ | OCH₃ | H | H | 4-(5-chloro-6-ethyl-pyrimidin-4-yloxy)-benzyl | |
| 57 | H | —CH₂OCH₃ | Cl | H | H | 4-tert-butylphenyl | |
| 58 | H | —CH₂OCH₃ | Cl | H | H | 4-(pyridin-4-yloxy)-benzyl | |
| 59 | H | —CH₂OCH₃ | Cl | H | H | 4-(4-cyano-phenoxy)-benzyl | |
| 60 | H | —CH₂OCH₃ | Cl | H | H | 4-(2,3,4,5,6-penta-fluorophenoxy)-benzyl | |
| 61 | H | CH₂OCH₃ | Cl | H | H | 4-tert-butyl-benzyl | |
| 62 | H | CH₂OCH₃ | Cl | H | H | 4-(4-cyano-phenoxy)-phenoxymethyl | |
| 63 | H | CH₂OCH₂CH₃ | Cl | H | H | 4-(4-chloro-phenoxy)-benzyl | |
| 64 | H | CH₂OCH₂CH₃ | OCH₃ | H | H | 4-(4-chloro-phenoxy)-benzyl | |
| 65 | H | CH₂OCH₃ | Cl | H | H | 4-(4,6-dimethoxy-[1,3,5]triazin-2-yloxy)-benzyl | |
| 66 | H | CH₂OCH₃ | Cl | H | H | 4-(2,4-dichloro-phenoxy)-benzyl | |
| 67 | H | CH₂OCH₃ | Cl | H | H | 4-cyclopentyl-benzyl | |
| 68 | H | CH₂OCH₃ | Cl | H | H | 2-[4-(4-chloro-phenoxy)-phenoxy- | |

TABLE 1-continued

| No. | A | R¹ | R² | R³ | R⁴ | Y—Z | Physical properties |
|---|---|---|---|---|---|---|---|
| | | | | | | ethyl | |
| 69 | H | CH₂OCH₃ | Cl | H | H | 4-(4-chloro-phenoxy)-phenoxymethyl | |
| 70 | H | CH₂OCH₃ | Cl | H | H | cis-4-methoxycyclohexyl | |
| 71 | H | CH₂OCH₃ | Cl | H | H | cis-4-(4-chloro-phenyl)-cyclohexyl | |
| 72 | H | CH₂OCH₃ | Cl | H | H | cis-4-phenyl-cyclohexyl | |
| 73 | H | CH₂OCH₂CH₃ | Cl | H | H | 4-(4-cyano-phenoxy)-benzyl | |
| 74 | H | CH₂OCH₃ | Cl | H | H | 4-butoxy-benzyl | |
| 75 | H | CH₂OCH₃ | Cl | H | H | 4-trifluoromethyl-benzyl | |
| 76 | H | CH₂OCH₃ | Cl | H | H | 4-trifluoromethoxy-benzyl | |
| 77 | H | CH₂OCH₃ | Cl | H | H | 4-(4-chloro-benzyloxy)-benzyl | |
| 78 | H | CH₂OCH₃ | Cl | H | H | 4-fluoro-benzyl | ¹H NMR(CDCl₃): δ= 3.45(s, 3H), 3.80 (s, 2H), 4.61(s, 2H), 7.12(m, 2H), 7.32 (m,2H), 7.90(s, 1H), 8.32(d, 1H), 8.40 (d, 1H). |
| 79 | H | CH₂OCH₃ | Cl | H | H | n-pentadecyl | |
| 80 | H | CH₂OCH₃ | Cl | H | H | 2-cyclohexyl-ethyl | |
| 81 | H | CH₂OCH₃ | Cl | H | H | 4-(6-chloro-benzothiazol-2-yloxy)-phenoxymethyl | |
| 82 | H | CH₂OCH₃ | OCH₃ | H | H | 4-(6-chloro-benzothiazol-2-yloxy)-phenoxymethyl | |
| 83 | H | CH₂OCH₃ | OCH₃ | H | H | 4-(2-chloro-4-trifluoromethyl-phenoxy)-phenoxymethyl | |
| 84 | H | CH₂OCH₃ | Cl | H | H | 4-[2-chloro-4-trifluoromethyl-phenoxy)-phenoxymethyl | |
| 85 | H | CH₂OCH₃ | Cl | H | H | 4-(2,4-dichlor-phenoxy)-phenoxymethyl | |
| 86 | H | CH₂OCH₃ | OCH₃ | H | H | 4-(2,4-dichlor-phenoxy)-phenoxymethyl | |
| 87 | H | CH₂OCH₃ | OCH₃ | H | H | 2-(4-fluoro-phenoxy)-ethyl | |
| 88 | H | CH₂OCH₃ | Cl | H | H | 2-(4-fluoro-phenoxy)-ethyl | |
| 89 | H | CH₂OCH₃ | CN | H | H | 2-(4-fluoro-phenoxy)-ethyl | |
| 90 | H | CH₂OCH₃ | OCH₃ | H | H | 4-(3-chloro-5-trifluoromethyl-pyridin-2-yloxy)-benzyl | |
| 91 | H | CH₂OCH₃ | Cl | H | H | 4-(3-chloro-5-trifluoromethyl-pyridin-2-yloxy)-benzyl | |
| 92 | H | CH₂OCH₃ | Cl | H | H | 4-phenoxy-benzyl | |
| 93 | H | CH₃ | COOEt | H | H | 4-phenoxy-benzyl | |
| 94 | H | CH₃ | COOEt | H | H | 4-(4-chloro-phenoxy)-benzyl | |
| 95 | H | CH₃ | COOEt | H | H | 4-(4-chloro-phenoxy)-phenoxymethyl | |
| 96 | H | CH₃ | COOEt | H | H | 4-(4-cyano-phenoxy)- | |

TABLE 1-continued

| No. | A | R¹ | R² | R³ | R⁴ | Y—Z | Physical properties |
|---|---|---|---|---|---|---|---|
| 97 | H | CH₃ | COOEt | H | H | 4-(4-nitro-phenoxy)-benzyl | |
| 98 | H | CH₃ | COOEt | H | H | 4-(2-chloro-4-tri-fluoromethyl-phenoxy)-phenoxy-methyl | |
| 99 | H | CH₃ | COOEt | H | H | 4-phenoxy-phenoxy-methyl | |
| 100 | H | CH₃ | COOEt | H | H | 2-[4-(4-chloro-phenoxy)-phenoxy]-ethyl | |
| 101 | H | CH₃ | COOEt | H | H | 2-(4-fluoro-phenoxy)-ethyl | |
| 102 | H | CH₃ | COOEt | H | H | 4-fluorobenzyl | |
| 103 | H | CH₃ | COOEt | H | H | 4-fluoro-phenoxy-methyl | |
| 104 | H | CH₃ | COOEt | H | H | 4-fluoro-phenyl | |
| 105 | H | CH₃ | COOEt | H | H | 4-(4-chloro-phenoxy)-phenyl | |
| 106 | H | CH₃ | COOEt | H | H | cis-4-(2-ethoxy-ethoxy)-cyclohexyl | |
| 107 | H | CH₃ | COOEt | H | H | Cis-4-(4-chloro-phenyl)-cyclohexyl | |
| 108 | H | CH₃ | COOEt | H | H | trans-4-(4-chloro-phenyl)-cyclohexyl | |
| 109 | H | CH₃ | COOEt | H | H | n-pentadecyl | |
| 110 | H | CH₃ | COOEt | H | H | cis-4-(2-methoxy-ethoxy)-cyclohexyl | |
| 111 | H | CH₃ | COOEt | H | H | 4-(4,6-dimethoxy-[1,3,5]triazin-2-yloxy)-benzyl | |
| 112 | H | CH₃ | COOEt | H | H | 4-(pyridin-4-yloxy)-benzyl | |
| 113 | H | CH₃ | COOEt | H | H | 4-(4,6-dimethoxy-pyridin-2-yloxy)-benzyl | |
| 114 | H | CH₃ | COOEt | H | H | 4-(4,6-dimethoxy-[1,3,5]triazin-2-yloxy)-benzyl | |
| 115 | H | CH₃ | COOEt | H | H | 4-(6-chloro-benzoxazol-2-yloxy)-benzyl | |
| 116 | H | CH₂OCH₃ | CN | H | H | 4-(6-chloro-benzoxazol-2-yloxy)-benzyl | |
| 117 | H | CH₂OCH₃ | CN | H | H | 4-(4,6-dimethoxy-pyrimidin-2-yloxy)-benzyl | |
| 118 | H | CH₂OCH₃ | CN | H | H | 4-(3-chloro-5-tri-fluoromethyl-pyridin-2-yloxy)-benzyl | |
| 119 | H | CH₂OCH₃ | CN | H | H | cis-4-tert-butyloxy-carbonyl-cyclohexyl | |
| 120 | H | CH₂OCH₃ | CN | H | H | cis-4-(2-methoxy-ethoxy)-cyclohexyl | |
| 121 | H | CH₂OCH₃ | CN | H | H | cis-4-ethoxy-cyclohexyl | |
| 122 | H | CH₂OCH₃ | CN | H | H | cis-4-tert-butyl-cyclohexyl | |
| 123 | H | CH₂OCH₃ | CN | H | H | 4-fluoro-phenoxy-methyl | |
| 124 | H | CH₂OCH₃ | CN | H | H | 4-fluoro-benzyl | |
| 125 | H | CH₂OCH₃ | CN | H | H | 4-(4-cyano-phenoxy)-benzyl | |
| 126 | H | CH₂OCH₃ | CN | H | H | 4-(4-nitro-phenoxy)- | |

TABLE 1-continued

| No. | A | R¹ | R² | R³ | R⁴ | Y—Z | Physical properties |
|---|---|---|---|---|---|---|---|
| | | | | | | benzyl | |
| 127 | H | CH₂OCH₃ | CN | H | H | 4-(2,3,4,5,6-pentafluorophenoxy)-phenoxymethyl | |
| 128 | H | CH₂OCH₃ | CN | H | H | 4-(4-chloro-phenoxy)-phenoxy)-methyl | |
| 129 | H | CH₂OCH₃ | CN | H | H | 2-(4-phenoxy-phenoxy)-ethyl | |
| 130 | H | CH₂OCH₃ | CN | H | H | 2-[4-(4-chloro-phenoxy)-phenoxy]-ethyl | |
| 131 | H | —CH₂OCH₃ | OCH₃ | H | H | 4-phenoxy-benzyl | ¹H NMR(CDCl₃): δ= 3.45(m,3H), 3.57 (s, 3H), 3.79(s, 2H), 4.53(s, 2H), 7.08 (m, 5H), 7.35(m, 4H), 7.90(s, 1H), 8.28 (m, 2H). |
| 132 | H | CH₂OCH₃ | CN | H | H | 4-(2-chloro-4-trifluoromethyl-phenoxy)-phenoxy-methyl | |
| 133 | H | CH₂OCH₃ | CN | H | H | 4-butoxy-benzyl | |
| 134 | H | CH₂OCH₃ | CN | H | H | 4-benzyloxy-benzyl | |
| 135 | H | CH₂OCH₃ | Br | H | H | 4-(4,6-dimethoxy-pyrimidin-2-yloxy)-benzyl | |
| 136 | H | CH₂CH₃ | I | H | H | 4-(4,6-dimethoxy-pyrimidin-2-yloxy)-benzyl | |
| 137 | H | CH₂CH₃ | I | H | H | 4-benzyloxy-benzyl | |
| 138 | H | CH₂CH₃ | I | H | H | 4-butoxy-benzyl | |
| 139 | H | CH₂CH₃ | I | H | H | 4-phenoxy-benzyl | |
| 140 | H | CH₂CH₃ | I | H | H | 4-trifluoromethoxy-benzyl | |
| 141 | H | CH₂CH₃ | I | H | H | 4-tert-butyl-benzyl | |
| 142 | H | CH₂CH₃ | I | H | H | 4-tert-butyl-phenyl | |
| 143 | H | CH₂CH₃ | I | H | H | cis-4-tert-butyl-cyclohexyl | |
| 144 | H | CH₂CH₃ | I | H | H | 4-fluoro-phenoxy-methyl | |
| 145 | H | CH₂CH₃ | I | H | H | 4-fluoro-benzyl | |
| 146 | H | CH₂CH₃ | I | H | H | 4-fluoro-phenyl | |
| 147 | H | CH₂CH₃ | I | H | H | 4-tert-butyl-phenyl | |
| 148 | H | CH₂CH₃ | I | H | H | 4-(4-chloro-phenoxy)-phenyl | |
| 149 | H | CH₂CH₃ | I | H | H | 4-phenoxy-phenyl | |
| 150 | H | CH₂CH₃ | I | H | H | 2-(4-fluoro-phenoxy)-ethyl | |
| 151 | H | CH₂CH₃ | I | H | H | 2-cyclopentyl-ethyl | |
| 152 | H | CH₂CH₃ | I | H | H | 4-cyclopentyl-benzyl | |
| 153 | H | CH₂CH₃ | I | H | H | biphenyl-4-ylmethyl | |
| 154 | H | CH₂OCH₃ | OCH₃ | H | H | biphenyl-4-ylmethyl | ¹H NMR(CDCl₃): δ= 3.40(s, 3H), 3.45 (s, 3H), 3.85(s, 2H), 4.50(s, 2H), 7.45 (m, 5H), 7.65(m, 4H), 7.91 (s, 1H), 8.29 (m, 2H). |
| 155 | H | CH₂CH₃ | CN | H | H | biphenyl-4-ylmethyl | |
| 156 | H | CH₂CH₃ | CN | H | H | 4-phenoxy-benzyl | |
| 157 | H | CH₂CH₃ | CN | H | H | 4-phenoxy-phenoxy-methyl | |
| 158 | H | CH₂CH₃ | CN | H | H | 4-(4-chloro-phenoxy)-phenoxymethyl | |
| 159 | H | CH₂CH₃ | CN | H | H | 2-(4-phenoxy- | |

TABLE 1-continued

[Structure: Pyridine ring with R¹ at 2-position, R² at 3-position, R⁴ at 6-position, R³ at 5-position, and N(A)-C(=O)-YZ at 4-position]

| No. | A | R¹ | R² | R³ | R⁴ | Y—Z | Physical properties |
|---|---|---|---|---|---|---|---|
| | | | | | | phenoxy)-ethyl | |
| 160 | H | CH₂CH₃ | CN | H | H | 2-[4-(4-chloro-phenoxy)-phenoxy)-ethyl | |
| 161 | H | CH₂CH₃ | CN | H | H | 4-cyclopentyl-benzyl | |
| 162 | H | CH₂CH₃ | CN | H | H | 4-fluoro-benzyl | |
| 163 | H | CH₂CH₃ | CN | H | H | 2-(4-fluoro-phenoxy)-ethyl | |
| 164 | H | —CH₂CH₃ | CN | H | H | 4-tert-butyl-benzyl | |
| 165 | H | —CH₂CH₃ | CN | H | H | 4-tert-butyl-phenyl | |
| 166 | H | —CH₂CH₃ | CN | H | H | (4-chloro-phenoxy)-phenyl | |
| 167 | H | —CH₂CH₃ | CN | H | H | 4-(4,6-dimethoxy-pyrimidin-2-yloxy)-benzyl | |
| 168 | H | —CH₂CH₃ | CN | H | H | 4-(2,3,4,5,6-pentafluorophenoxy)-benzyl | |
| 169 | H | —CH₂CH₃ | CN | H | H | 1-methyl-undecyl | |
| 170 | H | —CH₂CH₃ | CN | H | H | 1-methyl-decyl | |
| 171 | H | —CH₂OCH₃ | OCH₃ | H | H | 1-methyl-undecyl | |
| 172 | H | —CH₂OCH₃ | OCH₃ | H | H | 1-methyl-decyl | |
| 173 | H | —CH₂OCH₃ | Cl | H | H | 1-methyl-undecyl | |
| 174 | H | —CH₂OCH₃ | Cl | H | H | 1-methyl-decyl | |
| 175 | H | —CH₂OCH₃ | Cl | H | H | 1-methyl-undecyl | |
| 176 | H | —CH₂OCH₃ | CN | H | H | 1-methyl-decyl | |
| 177 | H | —CH₂OCH₃ | OCH₃ | H | H | 4-phenylmercapto-benzyl | |
| 178 | H | —CH₂OCH₃ | OCH₃ | H | H | 4-(4-tert-butyl-phenylmercapto)-benzyl | |
| 179 | H | —CH₂OCH₃ | OCH₃ | H | H | 4-(4-chlorophenyl-mercapto)-benzyl | |
| 180 | H | —CH₂OCH₃ | OCH₃ | H | H | 4-(4-chlorophenyl-mercapto)-benzyl | |
| 181 | H | CH₂OCH₂CH₃ | OCH₃ | H | H | 4-(4-chlorophenyl-mercapto)-benzyl | |
| 182 | H | —CH₂OCH₃ | OCH₃ | H | H | 4-(4-cyano-phenyl-mercapto)-benzyl | |
| 183 | H | —CH₂OCH₃ | OCH₃ | H | H | 4-(4-nitro-phenyl-mercapto)-benzyl | |
| 184 | H | —CH₂OCH₃ | Cl | H | H | 4-phenylmercapto-benzyl | |
| 185 | H | —CH₂OCH₃ | Cl | H | H | 4-(4-chlorophenyl mercapto)-benzyl | |
| 186 | H | —CH₂OCH₃ | Cl | H | H | 4-(4-cyano-phenyl-mercapto)-benzyl | |
| 187 | H | —CH₂OCH₃ | Cl | H | H | 4-(4-nitro-phenyl-mercapto)-benzyl | |
| 188 | H | —CH₂OCH₃ | CN | H | H | 4-phenylmercapto-benzyl | |
| 189 | H | —CH₂OCH₃ | CN | H | H | 4-(4-chloro-phenyl-mercapto-benzyl | |
| 190 | H | —CH₂OCH₃ | CN | H | H | 4-(4-cyano-phenylmer-capto)-benzyl | |
| 191 | H | —CH₂OCH₃ | CN | H | H | 4-(4-nitro-phenylmer-capto)-benzyl | |
| 192 | H | —CH₂CH₃ | I | H | H | 4-phenylmercapto-benzyl | |
| 193 | H | —CH₂CH₃ | I | H | H | 4-(4-chloro-phenyl-mercapto)-benzyl | |
| 194 | H | —CH₂CH₃ | I | H | H | 4-(4-cyano-phenyl-mercapto)-benzyl | |
| 195 | H | —CH₂CH₃ | I | H | H | 4-(4-nitro-phenyl-mercapto)-benzyl | |
| 196 | H | —CH₂OCH₃ | I | H | H | 4-(4-chloro-phenoxy)- | |

TABLE 1-continued

| No. | A | R¹ | R² | R³ | R⁴ | Y—Z | Physical properties |
|---|---|---|---|---|---|---|---|
| | | | | | | benzyl | |
| 197 | H | —CH₂OCH₃ | I | H | H | 4-(4-cyano-phenoxy)-benzyl | |
| 198 | H | —CH₂OCH₃ | I | H | H | 4-Benyloxy-benzyl | |
| 199 | H | —CH₂OCH₃ | I | H | H | biphenyl-4-ylmethyl | |
| 200 | H | —CH₂OCH₃ | I | H | H | 4-phenoxy-phenoxy-methyl | |
| 201 | H | —CH₂OCH₃ | I | H | H | 4-phenoxy-benzyl | |
| 202 | H | —CH₂OCH₃ | I | H | H | 4-(2,4-dichloro-phenoxy)-phenoxy-methyl | |
| 203 | H | —CH₂OCH₃ | I | H | H | 2-(4-phenoxy-phenoxy)-ethyl | |
| 204 | H | —CH₂OCH₃ | I | H | H | 2-(4-fluoro-phenoxy)-ethyl | |
| 205 | H | CH₂OCH₃ | I | H | H | 4-(6-chloro-benzoxa-zol-zyloxy)-benzyl | |
| 206 | H | CH₂OCH₃ | I | H | H | 4-(4,6-dimethoxy-pyrimidin-2-yloxy)-benzyl | |
| 207 | H | CH₂OCH₃ | I | H | H | 4-(3-chloro-5-trifluoromethyl-pyridin-2-yloxy)-benzyl | |
| 208 | H | CH₂OCH₃ | I | H | H | cis-4-tert-butyl-cyclohexyl | |
| 209 | H | CH₂OCH₃ | I | H | H | cis-4-(4-chloro-phenyl)-cyclohexyl | |
| 210 | H | CH₂OCH₃ | I | H | H | cis-4-phenyl-cyclo-hexyl | |
| 211 | H | CH₂OCH₃ | I | H | H | 4-fluoro-benzyl | |
| 212 | H | CH₂OCH₃ | I | H | H | 4-tert-butyl-benzyl | |
| 213 | H | CH₂OCH₃ | I | H | H | 4-(2,3,4,5,6-penta-fluorophenoxy-benzyl | |
| 214 | H | CH₂OCH₃ | I | H | H | 4-(2-chloro-4-tri-fluoromethyl-phenoxy)-phenoxy-methyl | |
| 215 | H | CH₂OCH₃ | I | H | H | 4-(butoxy-phenoxy-methyl | |
| 216 | H | CH₂OCH₃ | I | H | H | 4-(4-chloro-phenoxy)-phenyl | |
| 217 | H | CH₂OCH₃ | I | H | H | 4-tert-butyl-phenyl | |
| 218 | H | CH₂OCH₃ | I | H | H | 4-fluoro-phenyl | |
| 219 | H | CH₂OCH₃ | I | H | H | 4-phenoxy-phenyl | |
| 220 | H | CH₂OCH₃ | I | H | H | 1-methyl-decyl | |
| 221 | H | CH₂OCH₃ | I | H | H | 1-methyl-undecyl | |
| 222 | H | CH₂OCH₃ | I | H | H | 2-cyclopentyl-ethyl | |
| 223 | H | Cl | CN | H | H | 4-(4-chloro-phenoxy)-benzyl | m.p.: 197° C. |
| 224 | H | Cl | CN | H | H | 4-(4-cyano-phenoxy)-benzyl | |
| 225 | H | Cl | CN | H | H | 4-benzyloxy-benzyl | |
| 226 | H | Cl | CN | H | H | biphenyl-4-ylmethyl | |
| 227 | H | Cl | CN | H | H | 4-(4-chloro-phenoxy)-phenoxymethyl | |
| 228 | H | Cl | CN | H | H | 4-phenoxy-benzyl | |
| 229 | H | Cl | CN | H | H | 2-(4-fluoro-phenoxy)-ethyl | |
| 230 | H | Cl | CN | H | H | 4-(4,6-dimethoxy-pyrimidin-2-yloxy)-benzyl | |
| 231 | H | Cl | CN | H | H | cis-4-methyl-cyclo-hexyl | |
| 232 | H | Cl | CN | H | H | cis-4-tert-butyl-cyclohexyl | |

TABLE 1-continued

[Structure: pyridine with R¹, R², R³, R⁴ substituents and N(A)-C(=O)-YZ group]

| No. | A | R¹ | R² | R³ | R⁴ | Y—Z | Physical properties |
|---|---|---|---|---|---|---|---|
| 233 | H | Cl | CN | H | H | 4-tert-butyl-benzyl | |
| 234 | H | Cl | CN | H | H | 4-fluoro-benzyl | |
| 235 | H | Cl | CN | H | H | 4-butoxy-benzyl | |
| 236 | H | Cl | CN | H | H | 4-(2,3,4,5,6-penta-fluorophenoxy)-benzyl | |
| 237 | H | Cl | CN | H | H | 4-phenylmercapto-benzyl | |
| 238 | H | Cl | CN | H | H | 1-methyl-undecyl | |
| 239 | H | —OCH₃ | CN | H | H | 1-methyl-decyl | |
| 240 | H | —OCH₃ | CN | H | H | 4-(4-chloro-phenyl-mercapto)-benzyl | |
| 241 | H | —OCH₃ | CN | H | H | 4-(2,3,4,5,6-penta-fluorophenoxy-benzyl | |
| 242 | H | —OCH₃ | CN | H | H | 4-fluoro-benzyl | |
| 243 | H | —OCH₃ | CN | H | H | 4-tert-butyl-benzyl | |
| 244 | H | —OCH₃ | CN | H | H | cis-4-tert-n-butyl-cyclohexyl | |
| 245 | H | —OCH₃ | CN | H | H | cis-4-(4-chloro-phenyl-cyclohexyl | |
| 246 | H | —OCH₃ | CN | H | H | 4-(6-chloro-benzoxa-zol-2-yloxy)-benzyl | |
| 247 | H | —OCH₃ | CN | H | H | 4-(4,6-dimethoxy-pyrimidin-2-yloxy)-benzyl | |
| 248 | H | —OCH₃ | CN | H | H | 2-[4-(4-chloro-phenoxy)-phenoxy]-ethyl | |
| 249 | H | —OCH₃ | CN | H | H. | 4-(4-chloro-phenoxy)-phenoxymethyl | |
| 250 | H | —OCH₃ | CN | H | H | biphenyl-4-ylmethyl | |
| 251 | H | —OCH₃ | CN | H | H | naphthalen-2-ylmethyl | |
| 252 | H | —OCH₃ | CN | H | H | 4-benzyloxy-benzyl | |
| 253 | H | —OCH₃ | CN | H | H | 4-phenoxy-benzyl | m.p.: 146° C. |
| 254 | H | —OCH₃ | CN | H | H | 4-(4-chloro-phenoxy)-benzyl | m.p.: 168° C. |
| 255 | H | —OCH₃ | CN | H | H | 4-(4-nitro-phenoxy)-benzyl | |
| 256 | H | —OCH₃ | CN | H | H | 4-(4-cyano-phenoxy)-benzyl | |
| 257 | H | —CH₂OCH₃ | —OCH₃ | H | H | 4-(benzyloxy-phenoxy-methyl | ¹H NMR(CDCl₃): δ= 3.48 (s, 3H), 3.71 (s, 3H), 4.57 (s, 2H), 4.60(s, 2H), 5.03 (s, 2H), 8.34(m, 2H), 9.08(s, NH) |
| 258 | H | —CH₂OCH₃ | —OCH₃ | H | H | 4-Phenoxy-phenyl | ¹H NMR(CDCl₃): δ= 3.49 (s, 3H), 3.93 (s, 3H), 4.62 (s, 2H), 7.10–7.45(m,7H), 7.86(d, 2H), 8.36 (d, 1H), 8.42 (d, 1H), 8.60 (s, NH). |
| 259 | H | —CH₂OCH₃ | —OCH₃ | H | H | 4-(4-chloro-phenoxy)-cyclohexyl | ¹H NMR(CDCl₃): δ= 3.48(s, 3H), 3.88 (s, 3H), 4.2(m, 1H), 4.58(s, 2H), 6.83 (d, 2H), 7.20(d, 2H), 8.02(s, NH), 8.30 (m, 2H). |

We claim:
1. A compound of the formula I or an N-oxide or salt thereof

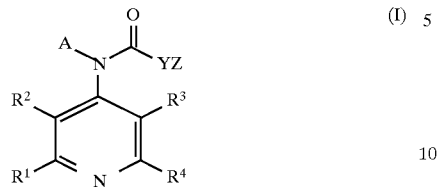

in which
- $R^1$ is $R-O(C_1-C_4)$alkyl, halo$(C_1-C_4)$alkoxy$(C_1-C_4)$alkyl, halo$(C_1-C_4)$alkoxy-halo$(C_1-C_4)$alkyl, $(C_1-C_4)$alkoxyhalo$(C_1-C_4)$alkyl, halo$(C_2-C_4)$alkenyloxy$(C_1-C_4)$alkyl, $(C_1-C_4)$alkylthio$(C_1-C_4)$alkylthio$(C_1-C_4)$alkyl, $(C_2-C_4)$alkenylthio$(C_1-C_4)$alkyl, halo$(C_1-C_4)$alkylthio$(C_1-C_4)$alkyl, $(C_1-C_4)$alkylthio-halo$(C_1-C_4)$alkyl, halo$(C_1-C_4)$alkylthio-halo$(C_1-C_4)$ or halo$(C_2-C_4)$alkenylthio$(C_1-C_4)$alkyl, $(C_1-C_4)$alkylthio, $(C_1-C_4)$alkylsulfinyl, $(C_1-C_4)$alkylsulfonyl, fluorine, chlorine, bromine, $(C_1-C_4)$alkyl, halo$(C_1-C_4)$alkyl, $(C_3-C_7)$cycloalkyl, $(C_1-C_4)$alkoxy or halo$(C_1-C_4)$alkoxy;
- $R^2$ is $(C_2-C_4)$alkenyloxy, $(C_2-C_4)$alkynyloxy, $(C_3-C_7)$cycloalkenyloxy, halo$(C_2-C_4)$alkenyloxy, halo$(C_3-C_7)$cycloalkyloxy, $R-O-CO-$, $(C_3-C_7)$cycloalkylthio, halo$(C_1-C_4)$alkylthio, $(C_3-C_7)$cycloalkylsulfinyl, halo$(C_1-C_4)$alkylsulfinyl, $(C_3-C_7)$cycloalkylsulfonyl, halogen$(C_1-C_4)$alkylsulfonyl, $(C_2-C_4)$alkenylthio, $(C_3-C_7)$cycloalkenylthio, $(C_2-C_4)$alkenylsulfinyl, $(C_3-C_7)$cycloalkenylsulfinyl, $(C_2-C_4)$alkenylsulfonyl, $(C_3-C_7)$cycloalkenylsulfonyl, iodine, cyano, $(C_1-C_4)$alkylthio, $(C_1-C_4)$alkylsulfinyl, $(C_1-C_4)$alkylsulfonyl, fluorine, chlorine, bromine, $(C_1-C_4)$alkyl, halo$(C_1-C_4)$alkyl, $(C_3-C_7)$cycloalkyl, $(C_1-C_4)$alkoxy or halo$(C_1-C_4)$alkoxy;
with the proviso that $R^1$ and $R^2$ are not both from the group consisting of $(C_1-C_4)$alkylthio, $(C_1-C_4)$alkylsulfinyl, $(C_1-C_4)$alkylsulfonyl, fluorine, chlorine, bromine, $(C_1-C_4)$alkyl, halo$(C_1-C_4)$alkyl, $(C_3-C_7)$cycloalkyl, $(C_1-C_4)$alkoxy and halo$(C_1-C_4)$alkoxy;
- $R^3$ and $R^4$ are identical or different and independently of one another are hydrogen, halogen, $(C_1-C_4)$alkyl, $(C_1-C_4)$haloalkyl, $(C_3-C_5)$cycloalkyl and/or halo$(C_3-C_5)$cycloalkyl;
- R is $(C_1-C_{10})$alkyl, $(C_2-C_{10})$alkenyl, $(C_2-C_{10})$alkynyl, $(C_3-C_8)$cycloalkyl or aralkyl;
- A is hydrogen, $(C_1-C_4)$alkyl, $(C_1-C_4)$acyl, aryl or aryl $(C_1-C_4)$alkyl wherein aryl is a phenyl group which is optionally substituted by one or more identical or different radicals selected from the group consisting of halogen, $(C_3-C_8)$cycloalkyl, $(C_3-C_8)$cycloalkenyl, phenoxy, substituted phenoxy, phenylthio, substituted phenylthio, phenyl, substituted phenyl, nitro, $-CO-R^8$, acetoxy, hydroxyl, cyano, $SiR^9R^{10}R^{11}$, $O-SiR^9R^{10}R^{11}$, $NR^{12}R^{13}$, $S(O)R^{14}$, $SO_2R^{14}$, optionally substituted $(C_1-C_{12})$alkyl, optionally substituted $(C_2-C12)$alkenyl, optionally substituted $(C_2-C_{12})$alkoxy, $(C_3-C_7)$cycloalkoxy, optionally substituted $(C_1-C_{12})$alkylthio and $(C_3-C_7)$cycloalkylthio, where in the above $(C_1-C_{12})$alkyl, $(C_2-C_{12})$alkenyl, $(C_1-C_{12})$alkoxy and $(C_1-C_{12})$alkylthio radicals one or more $CH_2$ groups are optionally replaced by CO and/or heteroatoms or heteroatom groups selected from the group consisting of O, S, SO, $SO_2$, $NR^5$ or $SiR^6R^7$ and where the optional substitutes are one or more identical or different radicals selected from the group consisting of halogen, halo$(C_1-C_4)$alkoxy, hydroxyl, $(C_3-C_8)$cycloalkyl, $(C_3-C_8)$cycloalkenyl, $(C_1-C_4)$acyl, phenyl, substituted phenyl, phenoxy, substituted phenoxy, phenylthio and substituted phenylthio; and
- $R^8$ is $(C_1-C_7)$alkyl, halo$(C_1-C_7)$alkyl, $(C_3-C_7)$cycloalkyl, halo$(C_3-C_7)$cycloalkyl, $(C_1-C_7)$alkoxy, $(C_1-C_7)$alkylthio, phenyl or substituted phenyl;
- $R^9$, $R^{10}$ and $R^{11}$ are identical or different and independently of one another are $(C_1-C_4)$alkyl, phenyl and/or substituted phenyl;
- $R^{12}$ and $R^{13}$ are identical or different and independently of one another are hydrogen, $(C_1-C_4)$alkyl and/or $(C_1-C_4)$acyl;
- $R^{14}$ is $(C_1-C_{10})$alkyl, phenyl or substituted phenyl;
- $R^5$ is hydrogen, $(C_1-C_4)$alkyl or $(C_1-C_4)$acyl;
- $R^6$ and $R^7$ identical or different, each independently are $(C_1-C_4)$alkyl, phenyl and/or substituted phenyl;
- Y-Z together is an optionally substituted $(C_1C_{15})$-hydrocarbon radical which is unbranched or branched and in which one or more $CH_2$ groups are optionally replaced by a heteroatom group, selected from the group consisting of O, $NR^5$, S, SO, $SO_2$ or $Si^6R^7$ wherein said radical is optionally substituted by one or more identical or different substituents and the substituents are selected from the group consisting of $(C_1-C_7)$alkyl, $(C_2-C_4)$alkenyl, $(C_2-C_4)$alkynyl, $(C_3-C_7)$cycloalkyl, $(C_3-C_7)$cycloalkenyl, halogen, halo$(C_1-C_4)$alkyl, halo$(C_3-C_7)$cycloalkyl, halo$(C_1-C_4)$alkoxy, halo$(C_3-C_7)$cycloalkoxy, hydroxyl, cyano and $(C_1-C_4)$acyl;
or, if not embraced by the above definitions,
- Y is a bond or a bivalent hydrocarbon radical having 1 to 6 carbon atoms which is optionally substituted by one or more identical or different radicals selected from the group consisting of $(C_1-C_7)$alkyl, $(C_2-C_4)$alkenyl, $(C_3-C_7)$alkynyl, $(C_3-C_7)$cycloalkyl, $(C_3-C_7)$cycloalkenyl, halogen, halo$(C_1-C_4)$alkyl, halo$(C_3-C_7)$cycloalkyl, halo$(C_1-C_4)$alkoxy, halo$(C_3-C_7)$cycloalkoxy, hydroxyl, cyano and $(C_1-C_4)$acyl; and
- Z is aryl as defined above;
or O-aryl if Y is not a direct bond;
or $(C_3-C_7)$cycloalkyl or $(C_5-C_8)$cycloalkenyl wherein one $CH_2$ group of the carbocycle is optionally replaced by $NR^{15}$ wherein $R^{15}$ is phenyl or substituted phenyl; and the above-mentioned $(C_3-C_8)$cycloalkyl or $C_5-C_8$)cycloalkenyl is optionally substituted by one or more identical or different radicals selected from the group consisting of $(C_1-C_{15})$alkyl, $(C_1-C_{16})$alkenyl, $(C_2-C_{18})$alkynyl, $(C_1-C_{12})$alkoxy, $(C_1-C_{12})$alkanoyloxy, $(C_2-C_{12})$acyl, $(C_1-C_{12})$alkyloxycarbonyl, $(C_1-C_{18})$alkanediyl, $(C_1-C_{18})$alkylidene, $SiR^9R^{10}R^{11}$, $NR^{16}R^{17}$, hydroxyl, oxo, halogen or aryl and wherein one or more $CH_2$ groups in the first 11 hydrocarbon radicals mentioned above are optionally replaced by a group selected from the group consisting of O, S, SO, $SO_2$, $NR^5$ or $SiR^6R^7$, where $R^5$, $R^6$ and $R^7$ are as defined above and where additionally three to six carbon atoms of these hydrocarbon radicals optionally form an optionally substituted cycle ring these hydrocarbon radicals, containing one or more identical or different substituents selected from the group consisting of halogen, haloalkyl, cycloalkyl, acyl, phenoxy, substituted phenoxy, phenyl, substituted phenyl, phenylthio and substituted phenylthio;
- $R^9$, $R^{10}$, $R^{11}$ and aryl are as defined above and $R^{16}$ and $R^{17}$ are identical or different and independently of one another are $(C_1-C_4)$acyl, $(C_3-C_6)$cycloalkyl, phenyl and/or substituted phenyl; or Z is a furyl radical of the formula II

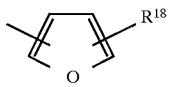  (II)

in which $R^{18}$ is hydrogen, halogen, halo$(C_1-C_4)$alkyl, cyano, nitro, $(C_1-C_4)$alkyl, phenyl, $(C_1-C_4)$alkoxy or halo$(C_1-C_4)$alkoxy; or Z is a thienyl radical of the formula III

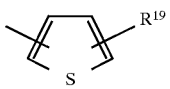  (III)

in which $R^{19}$ is hydrogen, halogen, halo$(C_1-C_4)$alkyl, cyano, nitro, $(C_1-C_4)$alkyl, phenyl, $(C_1-C_4)$alkoxy, halo$(C_1-C_4)$alkoxy or thienyl; or if not embraced by the above definitions, is a radical of the formula IV or V

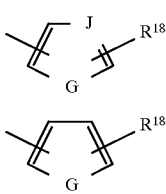  (IV)

(V)

in which $R^{19}$ is as defined above, J is N or CH and G is O, $NR^{20}$ or S, with the proviso that, if J≠N, then G is $NR^{20}$, where $R^{20}$ is hydrogen, $(C_1-C_4)$alkyl, $(C_1-C_4)$acyl, phenylsulfonyl or substituted phenyl-sulfonyl; or Z is a radical selected from the group consisting of optionally substituted naphthyl, dihydronaphthyl, tetrahydronaphthyl and decahydronaphthyl; or optionally substituted indolyl; or 1,3-benzodioxolyl, 2,6-dimethyl-4-morpholinyl and 1-adamantyl; or Z is a radical of the formula VI

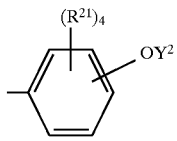  (VI)

in which $R^{21}$ radicals are identical or different and independently of one another are hydrogen, halogen, $(C_1-C_4)$alkyl, $(C_1-C_4)$alkoxy, halo$(C_1-C_4)$alkyl, halo$(C_1-C_4)$alkoxy, $NO_2$, CN, $(C_1-C_4)$alkylcarbonyl, formyl, phenoxy and/or substituted phenoxy, with the proviso that at least two of the radicals $R^{21}$ are selected from the group consisting of hydrogen and fluorine, and $Y^2$ is pyridyl, pyrazinyl, pyrimidinyl, pyridazinyl, triazinyl, benzoxazolyl or benzothiazolyl, which are optionally substituted by one or more identical or different radicals selected from the group consisting of halogen, $(C_1-C_4)$alkyl, $(C_1-C_4)$alkoxy, halo$(C_1-C_4)$alkyl, halo$(C_1-C_4)$alkoxy, nitro, cyano and $(C_1-C_4)$alkanoyl; or Z is a radical of the formula VII

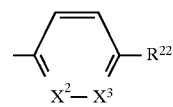  (VII)

in which one of the groups $X^2$ or $X^3$ is N, and the other group is CH;

$R^{22}$ is —W—$R^{23}$, phenyl or substituted phenyl;

W is O or S; and $R^{23}$ is $(C_1-C_7)$alkyl, halo$(C_1-C_7)$alkyl, $(C_1-C_7)$alkoxy, halo$(C_1-C_7)$alkoxy, naphthyl or phenyl, where, if not embraced by the above definitions, each of the abovementioned radicals are optionally substituted by one or more identical or different radicals selected from the group consisting of halogen, $(C_1-C_{10})$alkyl, halo$(C_1-C_7)$alkyl, hydroxy$(C_1-C_7)$alkyl, $(C_1-C_4)$alkoxymethyl, $(C_1-C_4)$alkoxy, halo$(C_1-C_4)$alkoxy, phenoxy, substituted phenoxy, phenyl, substituted phenyl, cyano, nitro, hydroxyl, $(C_1-C_4)$alkanoyloxy or benzyloxy.

2. A compound according to claim 1 or an N-oxide or salt thereof wherein $R^1$ is $(C_1-C_2)$alkoxymethyl, halomethoxymethyl, halomethoxyhalomethyl, methoxyhalomethyl, fluorine, chlorine, bromine, $(C_1-C_4)$alkyl, halo$(C_1-C_2)$alkyl, cyclopropyl, methoxy or ethoxy;

$R^2$ is fluorine, chlorine, iodine, cyano, cyclopropyl, $(C_1-C_4)$alkyl, halo$(C_1-C_2)$alkyl; cyclopropyl, methoxy, or ethoxy;

$R^3$ and $R^4$ are identical or different, independently of one another are hydrogen or fluorine.

3. A compound according to claim 1 or an N-oxide or salt thereof wherein $R^1$ is methoxymethyl, chlorine, bromine, ethyl, propyl, isopropyl, trifluoromethyl, or methoxy;

$R^2$ is chlorine, bromine, iodine, cyano, ethyl, propyl, isopropyl, trifluoromethyl or methoxy.

4. A compound according to claim 1 or an N-oxide or salt thereof wherein

Y-Z is an optionally substituted $(C_1-C_{15})$hydrocarbon radical which is unbranched or branched and in which one ore more $CH_2$ groups are optionally replaced by a heteroatom group selected from the group consisting of O, $NR^5$, S, SO, $SO_2$ or $SiR^6R^7$, wherein said radical is optionally substituted by one or more identical or different substituents selected from the group consisting of $(C_1-C_4)$alkyl, halogen, halo$(C_1-C_4)$alkyl and halo$(C_1-C_4)$alkoxy;

or, if not embraced by the above definitions;

Y is a bond or a bivalent hydrocarbon radical having 1 to 4 carbon atoms which is optionally substituted by one or more identical or different radicals selected from the group consisting of $(C_1-C_4)$alkyl, halogen, halo $(C_1-C_4)$alkyl and halo$(C_1-C_4)$alkoxy; and Z is aryl, where aryl is a phenyl group which is optionally substituted by one or more identical or different radicals selected from the group consisting of halogen, $(C_3-C_8)$cycloalkyl, phenoxy, substituted phenoxy, phenylthio, substituted phenylthio, phenyl, substituted phenyl, and optionally substituted $(C_1-C_{12})$alkyl, optionally substituted $(C_2-C_{12})$alkenyl, optionally substituted $(C_1-C_{12})$alkoxy and optionally substituted $(C_1-C_{12})$alkylthio, wherein the above $(C_1-C_{12})$alkyl, $(C_2-C_{12})$alkenyl, $(C_1-C_{12})$alkoxy and $(C_1-C_{12})$alkylthio one or more $CH_2$ groups are optionally replaced by CO and/or heteroatoms or heteroatom groups selected from the group consisting of O, S, SO, $SO_2$, $NR^5$ or $SiR^6R^7$ and wherein the optional substitutes are one or more identical or different radicals selected from the group consisting of halogen, phenyl, substituted phenyl, phenoxy, substituted phenoxy, phenylthio and substituted phenylthio; and Z is also O-aryl if Y is not a direct bond; aryl being as defined above; or Z is cyclohexyl which is substituted by one or more radicals selected from the group consisting of $(C_1-C_{18})$alkyl, $(C_2-C_{18})$alkynyl, $(C_1C_{12})$alkoxy, $(C_1-C_{12})$alkanoyloxy, $(C_1-C_{12})$alkyloxycarbonyl, $SiR^9R^{10}R^{11}$ and aryl and wherein one or more $CH_2$ groups in the first 6 hydrocarbon radicals mentioned above are optionally replaced by O, and wherein additionally 3 to 6 carbon atoms of these hydrocarbon radicals optionally form a cycle ring; or Z is a radical selected from the group consisting of optionally substituted naphthyl and optionally substituted tetrahydronaphthyl; or Z is a radical of the formula VI in which $R^{21}$ radicals are identical or different and independently of one another are hydrogen, halogen and/or methyl, with the proviso that at least two of the radicals $R^{21}$ are selected from the group consisting of hydrogen and fluorine; and $Y^2$ is pyridyl, pyrazinyl, pyrimidinyl, pyridazinyl, triazinyl, benzoxazolyl or benzothiazolyl, which are optionally substituted by one or more identical or different radicals selected from the group consisting of halogen, methyl, methoxy and trifluoromethyl.

5. A compound according to claim 1 or an N-oxide or salt thereof wherein

Y-Z together is an optionally substituted $(C_1-C_{15})$ hydrocarbon radical which is unbranched or branched and in which one or more $CH_2$ are optionally replaced by O or S; said radical substituted by one or more identical or different substituents selected from the group consisting of methyl, ethyl, fluorine, chlorine and trifluoromethyl;

or, if not embraced by the above definitions,

Y is a bond or a bivalent hydrocarbon radical having 1 to 2 carbon atoms which is substituted by one or more identical or different radicals selected from the group consisting of methyl, ethyl, fluorine, chlorine and trifluoromethyl; and Z is aryl, where the aryl is a phenyl group which is optionally substituted by one or more, identical or different, radicals selected from the group consisting of phenoxy, substituted phenoxy, phenylthio, substituted phenylthio, optionally substituted $(C_1-C_{12})$alkoxy and optionally substituted $(C_1-C_{12})$alkylthio, where in the above $(C_1-C_{12})$alkoxy and $(C_1-C_{12})$alkylthio one or more $CH_2$ groups are optionally replaced by O and the optional substitutes are one or more identical or different radicals selected from the group consisting of halogen, phenyl, substituted phenyl, phenoxy and substituted phenoxy; or Z O-aryl if Y is not a direct bond; or Z is cyclohexyl which is substituted in the 4-position by a radical selected from the group consisting of $(C_3-C_{18})$alkyl or aryl; or Z is a group of the formula VI

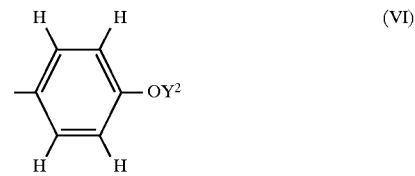

any $Y^2$ is pyridyl, pyrimidinyl, triazinyl and benzoxazolyl and is optionally substituted by one or more identical or different radicals selected from the group consisting of fluorine, chlorine, trifluoromethyl, methyl or methoxy.

6. A process for the preparation of a compound of the formula I as claimed in claim 1, which comprises reacting a compound of the formula VIII

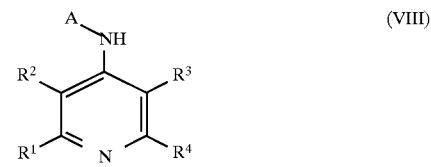

in which A, $R^1$, $R^2$, $R^3$ and $R^4$ are as defined in claim 1, with a compound of the formula IX

in which Y and Z are as defined in claim 1 and L is a leaving group, and, if appropriate, converting the resulting compound of the formula I into an N-oxide or into a salt thereof.

7. A composition comprising at least one compound as claimed in claim 1 and at least one formulation auxiliary.

8. A fungicidal composition, comprising a fungicidally effective amount of at least one compound as claimed in claim 1 together with the additives or auxiliaries which are customary for this application.

9. An insecticidal, acaricidal, ixodicidal or nematicidal composition, comprising an effective amount of at least one compound as claimed in claim 1 together with the additives or auxiliaries customary for this application.

10. A crop protection product comprising a fungicidally, insecticidally, acaricidally, ixodicidally or nematicidally effective amount of at least one compound as claimed in claim 1 and at least one further active substance, preferably selected from the group consisting of the fungicides, insecticides, attractants, sterilants, acaricides, nematicides and herbicides, together with the auxiliaries and additives customary for this application.

11. A composition for use in the protection of wood or as a preservative in sealants, in paints, in cooling lubricants for metal working or in drilling and cutting oils, comprising an effective amount of at least one compound as claimed in claim 1 together with the auxiliaries and additives customary for these applications.

12. A pharmaceutical preparation for controlling endo- or ectoparasites comprising an amount of a compound as claimed in claim 1 which is effective for this application, together with a pharmaceutically acceptable excipient.

13. A method of controlling phytopathogenic fungi, which comprises applying a fungicidally active amount of a compound as claimed in claim 1 to these fungi, to the plants, areas or substrates infected with them or to seed.

14. A method of controlling harmful insects, Acarina, mollusks, nematodes in which an effective amount of a compound as claimed in claim 1 is applied to these harmful insects, Acarina, mollusks and nematodes or to the plants, areas or substrates infested with them.

15. A method of controlling endo- or ectoparasites, comprising the administration of an amount of a compound as claimed in claim 1 which is effective for this purpose.

16. Seed, treated or coated with an effective amount of a compound as claimed in claim 1.

* * * * *